Figure 1A:
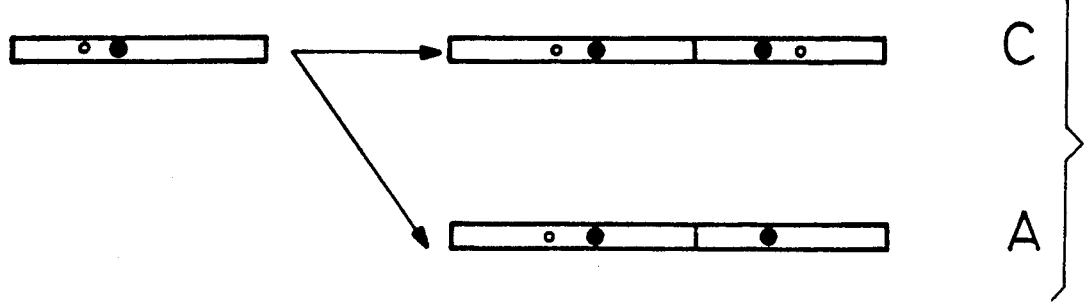
Figure 1B:
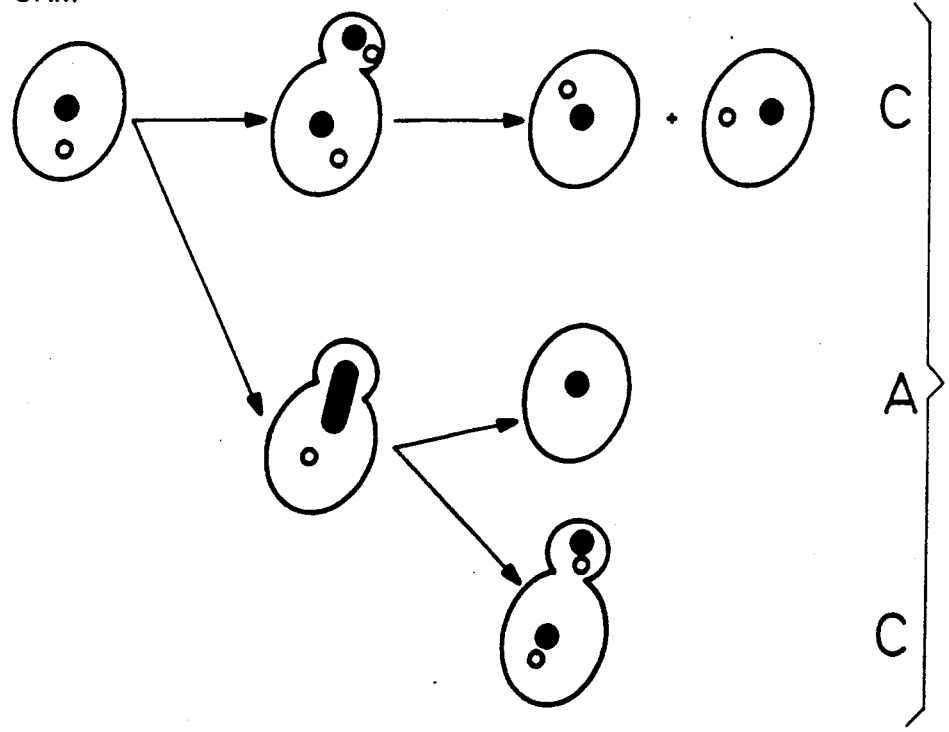
Figure 2A:
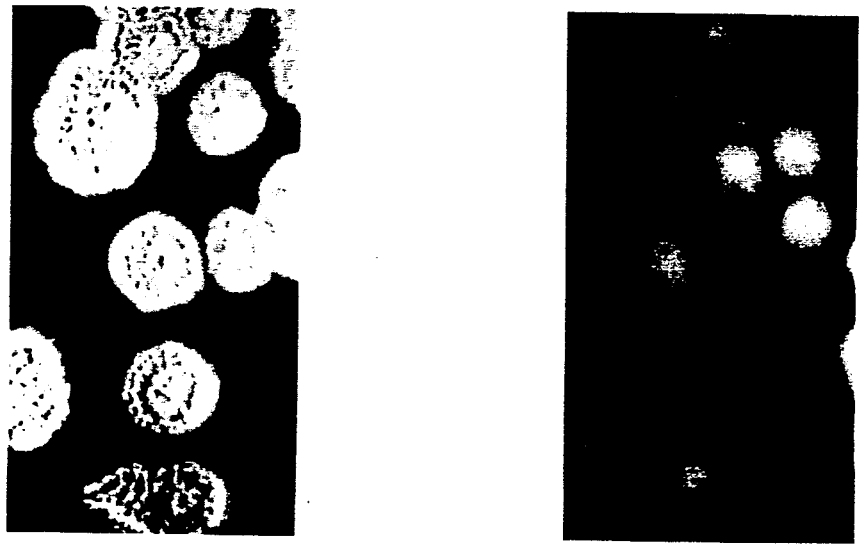
Figure 2B:
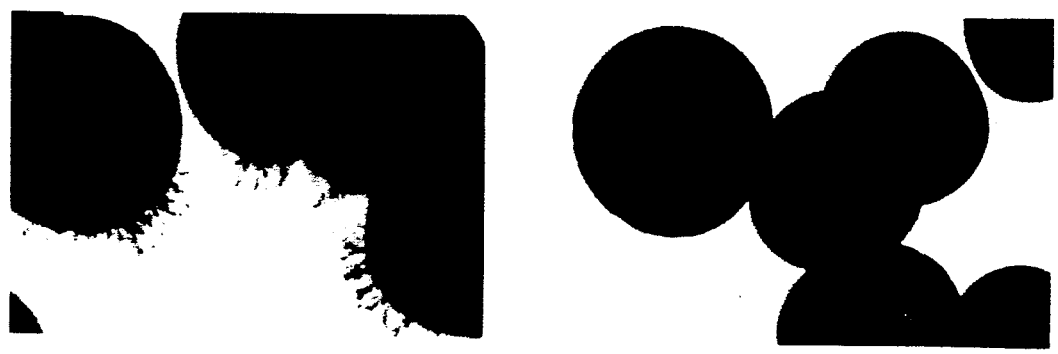
Figure 3A:
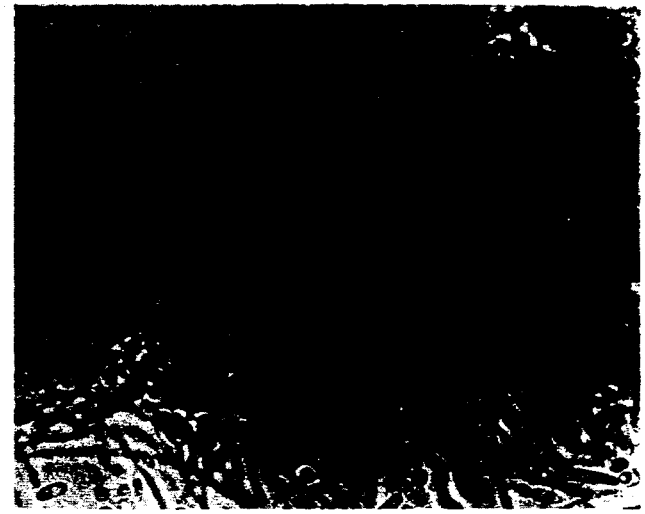
Figure 3B:

United States Patent [19]

Fournier et al.

[11] Patent Number: 5,212,087
[45] Date of Patent: May 18, 1993

[54] ARS SEQUENCE WHICH IS EFFICACIOUS IN YARROWIA LIPOLYTICA

[75] Inventors: Phillippe Fournier, Paris; Claude Gaillardin, Versailles; Bernard Kudla; Henri Heslot, both of Paris, all of France

[73] Assignee: Institut National de la Recherche Agronomique (INRA), Paris, France

[21] Appl. No.: 303,874

[22] Filed: Jan. 27, 1989

[30] Foreign Application Priority Data

Jan. 28, 1988 [FR] France ................. 88 00973

[51] Int. Cl.$^5$ .............. C12N 1/19; C12N 15/11; C12N 15/81
[52] U.S. Cl. .................. 435/255; 435/69.1; 435/69.4; 435/69.5; 435/69.51; 435/172.3; 435/256; 435/320.1; 536/23.1; 935/14; 935/37; 935/56; 935/69
[58] Field of Search .......... 435/172.3, 255, 256, 435/320.1, 69.1, 69.5, 69.4, 212, 69.51; 536/27; 935/37, 69, 56, 14

[56] References Cited

FOREIGN PATENT DOCUMENTS 045573 7/1981 European Pat. Off. .
138508 3/1984 European Pat. Off. .
166659 6/1985 European Pat. Off. .
180899 10/1985 European Pat. Off. .
220864 10/1986 European Pat. Off. .

OTHER PUBLICATIONS

Wing et al., Diss Abst. vol. 49, No. 7, Oct. 1988, p. 1011 B "Development of the molecular biology of the yeast Yarrowia lipolyticai I. Development of a transformation system and search for autonomously replicating sequences. II. Cloning and sequencing of the alkaline extra cellular protease structural gene" (University of California, Davis, 1987).

Primary Examiner—Richard A. Schwartz
Assistant Examiner—J. Leguyader
Attorney, Agent, or Firm—Cooley, Godward, Castro, Huddleson & Tatum

[57] ABSTRACT

The present invention relates to ars sequences which are efficacious in *Yarrowia lipolytica*, as well as to plasmids carrying these sequences.

The strains of *Y. lipolytica* transformed with the said plasmids may be used in fermentation processes enabling proteins of industrial importance to be prepared.

25 Claims, 20 Drawing Sheets

MYCELIAL FORM

YEAST FORM

PARENT　　　　MUTANT

FIG.8A
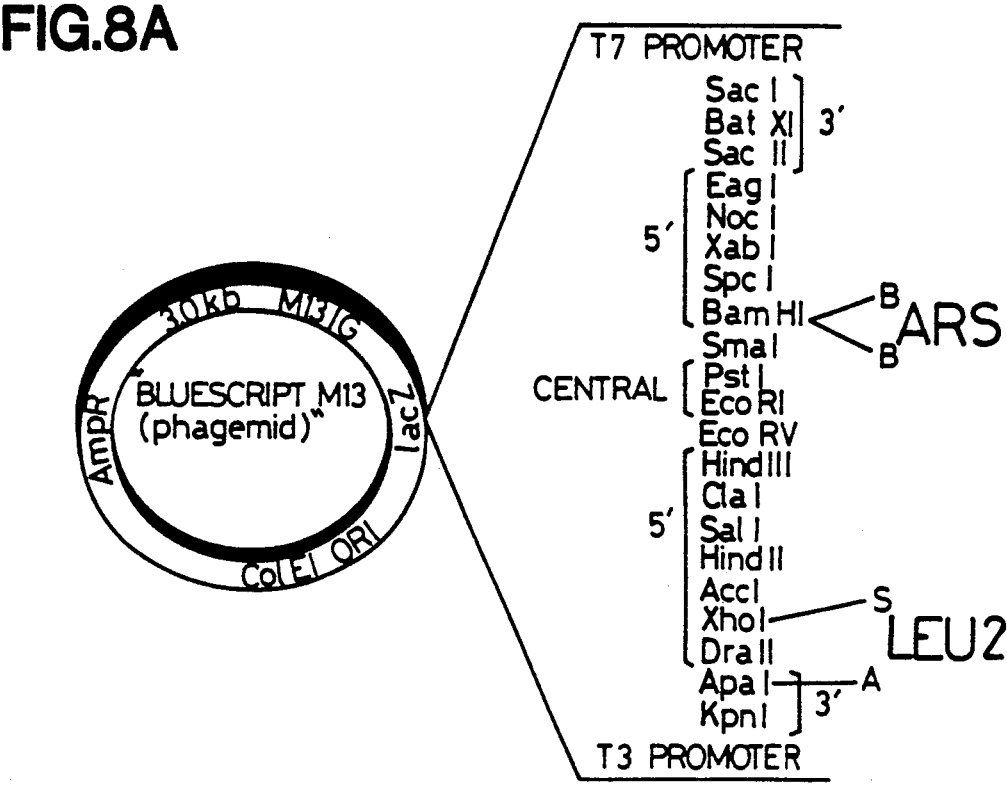
FIG.8B
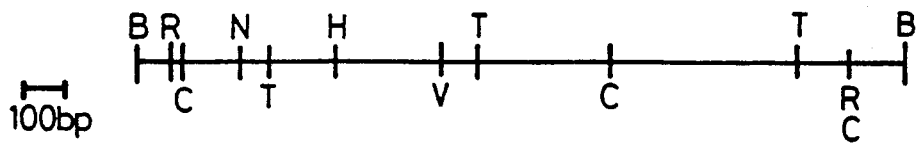
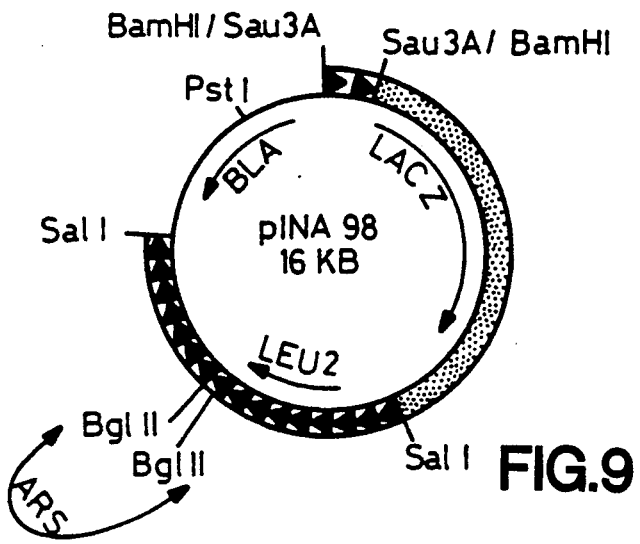
FIG.9

```
BamHI
GGATCCCAAT ATTACACCCA AGTAGCATGC ATAAGCTAAA AGTAACTCGC AGCGCACACC    60

GTGCAGATTC ATAAGTCTAT GATTAATTGA ACGCCAATAA CCCGGCTTAC TACAAGTACA   120
                                                  J-10

AGTAGGTATA CATAGCGGTA ATGAATCATT AGAAAAAAAA AAAACAAAAA AAAACAAAAC   180
                H-11
                       F-10

AAACTGTTGT GGATGCATCA ACAGTAGTAC ATAGTTGTAC GATGTACTTG TACTTGTAAA   240
                                              AsuII

AGCAAAAATG TACAATATCT CAGGGAGCGC AACTTTTACG TTCGAAGAAC AATGTACCGC   300

ATACCGCATT CTAGATTCTG CGGAACGTCT AACCTGGAAA TACGATTTTT TTTTTCTTTC   360

ATTTTTTTTG CTTCTTCAAA AGTATGGTAA TTTCCTACCA TTACAGTTGA CACTGAACGA   420
                                  L-10

GGGGGGATTG AATTTAAGCA AAAAATTAAA TCAAAATACC TTTATGTATC CAGCCCATGT   480
                                                     Sau3A

AATAAACAAA AGGATTATAT AACAAGAAAT AAATATATAC CTTTAATGGA TCATTAGAAT   540
               D-11
               K-10          HindIII    L-10        F-10

AAAAATAAAT ACGAGAAGCA CACCAGAGAA GCTTTTGAT TGCCACTATA CCGCTACTTT    600
    E-11

GGTATATCTT ATTATAATTG TTGAATTTGC AAGATAGAAT GTCATTCATT GGAGAGAAAT   660
```

FIG. 13A

```
CCAAGGAATA TGTGGGATGA AATGACTAGA AGTATGAACA ATGAGAATAG TACATACTTG      720

TACCTGTATT TCTAGAAGAG AGAAAGACAG TTGAGTGTGT GATTCTCGTC CAATAATAAT      780
                                                          M-10
CTCAATAGTA ACGTGTGAAT AGCTGTTCTT TGATAGTTGA TATTTCTCGA TGACTATTTA      840
                                    AsuI I                  EcoRV
TGTTGTACAA GGGATTTTTT TCGTTGCTGT TGATTTCGAA TTAGGCAATG CAGATATCAT      900

TTATGCTATC CATATTTAAG ATTTCCCATA CGCATTTATA ACATTTATTC TACATAAATT      960
                                                           G-10
GTTAAATGAA CGAACTGCCA TTATAAATTG TTTCCTAAAT AGAAGTGTT TTTCATAAAG      1020
 G-10   I-10             G-10
CAAGTAAGTT GTCTAATAAT ACTAAGTAAT AAAAATAAGT TCATACAATA TATTTTGAGA     1080
 I-10       M-10          E-11                K-10      A-12
                H-11                                         J-10
ACATCATTTG GAGGCGGTAG ATGGAGTCTG TTTATTATTA AACAATGCGA GATGACCCCT     1140
 J-10    B-10         C-13
TAAATATTGA GAACATCAGT TGGAGGCGGC AGATGGAGTC TGTCTATTTA GCAATGGGAC     1200
  A-12        B-10         C-13

ATGACTGTCA GTATCATCAT GATGTATATA TATAATACAT ATAATATTAT ATAACACGAT     1260
                      Sau3A               D-11
TTTTTTAAAT TATTGGCCCG AAAATTAATC AGTGTAGACT GGATC  1305
```

FIG. 13B

ARS SEQUENCE WHICH IS EFFICACIOUS IN YARROWIA LIPOLYTICA

The present invention relates to autonomously replicating sequences in *Yarrowia lipolytica*, to processes for preparing them and to their use in processes employing recombinant DNAs.

The existence, the role and the cloning of sequences conferring autonomy of replication on yeast plasmids has been well documented in *Saccharomyces cerevisiae* (1,2). A bacterial plasmid (type pBR322) in which a yeast marker gene (for example a gene coding for a biosynthetic enzyme, such as LEU2, URA3, LYS2, TRP1, and the like) has been cloned is capable of integrating at low frequency in the chromosome, most often by homologous recombination at the locus in question. If a so-called ars (for autonomously replicating sequence) sequence is introduced into such a plasmid, the transformation then assumes the following features:

high efficacy (more than 10,000 transformants/1 g of DNA)
extrachromosomal replication of the plasmids,
relative instability in mitosis.

The ars sequences are DNA sequences, either of the same species or of different species. They can be of chromosomal or extrachromosomal origin (plasmids, mitochondria, etc.). However, the reviews produced by several authors (1,2) show clearly that, in most cases, the sequences manifesting an ars property in a heterologous host do not have this characteristic in the initial organism. In a homologous context, the most commonly accepted hypothesis is that the ars sequences isolated from the chromosome correspond to the origins of replication, which are considered to be spaced on average 20 to 40 kb apart on yeast chromosomes.

In the industrial yeast *Yarrowia lipolytica*, integrative transformation has been described with the LYS2 gene of *S. cerevisiae* (3) and the LEU2 gene of *Y. lipolytica* (4). The promoter of this same gene has been used (5) to direct the expression of heterologous genes (resistance to phleomycin and beta-galactosidase) integrated in the chromosome at the leu2 locus. Moreover, it has been shown (4) that, when the transforming plasmid is linearized with a restriction enzyme possessing only one cleavage site, the frequency of transformation is increased by a factor of 100 (the frequency is then changed from fewer than 100 to more than 10,000 transformants per 1 g of DNA). This recombinogenic effect of the cohesive ends generated by a restriction enzyme, already known in *S. cerevisiae*, is much more pronounced in *Y. lipolytica*.

When it is desired to clone a gene by complementation using integrative transformation in *Y. lipolytica*, the following difficulties are encountered:

(a) since the DNA library is produced in an integrative plasmid of the pBR322+LEU2 type, it is not known whether the restriction sites present only once in this plasmid are not also present in the cloned fragments; accordingly, to linearize the DNA, it becomes obligatory to perform partial restrictions (and to carry out this test with different enzymes) whose transformation efficacy is lower;

(b) when the clones have been obtained by complimentation, a fine analysis must be performed of the restriction map of the cloned fragment integrated in the genome, using Southern's technique and radioactive probes; the study of this map provides the information as to which enzyme may be used to cut the total DNA of the transformant in order to extract the plasmid, which is selected, after ligation, by transformation in *Escherichia coli*.

These two drawbacks are eliminated if the DNA library can be produced in a replicative plasmid containing an ars sequence; in effect, it is, under these circumstances, pointless to cut the plasmid with a restriction enzyme, and the plasmid, being maintained extrachromosomally, may be readily recovered in *E. coli*. The presence of an ars sequence also makes it possible, in principle, to amplify a gene, since plasmids are generally present in multicopy form. All these reasons have justified the search for an ars for *Yarrowia lipolytica*.

Since several attempts at selection have met, in several laboratories, with failure (6), the hypothesis has been put forward that the mode of cell division of this yeast could be responsible for this. In effect (FIG. 1), *Y. lipolytica* is dimorphic, producing both mycelium and yeast-shaped forms. It has been shown in *S. cerevisiae* (7) that ars plasmids show a strong maternal propensity for segregation, that is to say, all the copies tend to segregate as a block and do not pass systematically to the daughter cell. If the latter is a bud from a yeast-shaped cell, it will admittedly cease to divide in selective medium, but the mother cell will still have the possibility of transmitting the plasmid during a subsequent division (in *S. cerevisiae*, a mother cell can divide some twenty times). On the other hand, if a mycelial product is involved, each cell gives rise to only one daughter cell. If the plasmid is not passed during a division, the colony ceases to divide in selective medium. On the basis of this hypothesis, mutants have hence been selected which are incapable of forming mycelium, and they have been used in the search for ars sequences. Such sequences have been effectively isolated, and they have also proved to be functional in cells of the mycelial type.

The present invention relates to an ars sequence which is efficacious in *Yarrowia lipolytica*, as well as to a DNA sequence containing such an ars sequence. In particular, the present invention relates to the ars sequence which is efficacious in *Y. lipolytica* carried by the 2.2 kb BamHI/BamHI DNA fragment possessing the restriction map of FIG. 8B, as well as to the plasmids containing these sequences.

The present invention relates more especially to a plasmid carrying an ars sequence which is efficacious in *Yarrowia lipolytica*, and which may be obtained, in particular, by the following process:

a) a library of genomic fragments of *Y. lipolytica* is formed in an integrative vector complementing an auxotrophy of *Y. lipolytica*;
b) a host strain of *Y. lipolytica*, possessing an auxotrophy capable of being complemented by the above integrative vector, is transformed with the plasmids of the above library;
c) colony hybridization is performed with a probe which detects the integrative vector, and the transformants possessing the strongest signal are selected;
d) a minilysate of the vector clones is prepared and the extrachromosomal plasmids are detected;
e) these plasmids carry an ars sequence, which may be confirmed by testing their power of transformation, which is at least 5 times as great as the power of transformation of the original vector.

As will be recalled in the examples, *Y. lipolytica* colonies show different morphologies at the macroscopic level, namely so-called "fuzzy" or rough colonies forming skins and surrounded by tufts at the surface of the agar, this morphology being more distinct when the cells are not too numerous per dish, and, on the other hand, so-called "unfuzzy" colonies which do not show these characteristics.

The fuzzy phenotype will be designated in that which follows "Fil+", and the corresponding genotype "fil+".

As will emerge from the examples, in the case where the receptor strain is a Fil− strain, it is possible between the stages b and c to test the stability of the transformants and to select the transformants possessing the lowest stability. In effect, this was the process used for the selection of the first ars sequences. However, when Fil+ strains are used, it is preferable to use the process described above.

It is appropriate to note that, obviously, this process can undergo many modifications while leading, in each case, to the selection of plasmids carrying the ars sequence.

Preferably, the process according to the present invention will be carried out in the following manner:

formation of a library of genomic fragments of *Y. lipolytica* in an integrative vector of pINA62 type;

transformation of supercoiled circular plasmids of this library in a Fil+ strain, selection of the LEU+ transformants (can contain an integrated plasmid or replicative plasmids);

colony hybridization with a pBR322 probe: it is expected that a stronger signal will be found in the multicopy replicative transformants; isolation of potential ars clones;

minilysates of the clones selected, Southern transfer of non-restricted DNA: detection of extrachromosomal plasmids with a pBR322 probe;

transformation of *E. coli* with the DNA of the minilysates and amplification of the ars plasmids;

characterization, where appropriate, of the instability of the clones.

The process described above naturally corresponds to the use of specific vectors derived from pBR322, such as pINA62.

The different techniques which are mentioned in this process, as in the general process, are well known to those versed in the art, and they will be described in greater detail in the attached examples, without it being possible for these detailed characteristics to be considered to be decisive for carrying out the present invention.

As will also be described in the examples, it is possible, from the plasmids containing the ars sequences, to perform an isolation of the sequences or at least of larger sequences carrying the ars sequence. These sequences thus isolated, or even isolated plasmid fragments, are usable for the production of expression vector plasmids, since the presence of these ars sequences enables the said plasmids to be maintained in the extrachromosomal state and to be capable of amplification, this leading to an overproduction of the protein expressed by the said plasmid.

Various expression vectors have already been described in the prior art, especially in European Patent No. 0,220,864, as well as European Patents No. 0,138,508 and No. 0,166,659.

These various patents describe, in essence, so-called integration vectors, the drawbacks of which have been mentioned previously. However, these integration vectors may be converted to extrachromosomal plasmids if the ars sequences described above are attached to them.

The technology of expression vectors will not be described in detail; in effect, this technology is already widely described in the above patents, both as regards the elements for the expression of genes in *Y. lipolytica*, especially the promoters which can be *Y. lipolytica* promoters, for example the promoters of the XPR2 or LEU2 genes, and as regards the types of genes which can be cloned. Among the genes which can be cloned, there should be mentioned, for example, the genes coding for prorennin and human anaphylatoxin C5a, as is described in European Patent No. 0,220,864, and also alkaline extracellular protease (AEP), invertase, porcine interferon-alpha$_1$ or prochymosin.

By way of example, in the context of the present invention, mention will be made only of the expression of beta-galactosidase in order to show the efficacy of the corresponding ars sequences, but it would obviously be perfectly possible to perform the same type of construction by using the plasmids described in European Patent No. 0,220,864 and attaching the ars sequence to them.

The present invention hence also relates, besides the DNA sequences carrying an ars sequence which is efficacious in *Y. lipolytica*, to the plasmids incorporating the said sequence, and especially the plasmids for the expression of an industrial protein.

These plasmids for the expression of an industrial protein in *Y. lipolytica* contain, besides the sequence coding for the said protein, all the elements, in particular a control region containing a promoter, enabling provision to be made for the expression of the said proteins in *Y. lipolytica*, and contain, in addition, an ars sequence.

It can, in addition, be advantageous to have at one's disposal an integration plasmid containing this type of ars sequence and capable of complementing an auxotrophy of *Y. lipolytica*.

The invention also relates to the strain of *Y. lipolytica* transformed by a plasmid as described above, it being possible for this strain to be Fil+ or Fil−.

Finally, the present invention relates to a process for preparing an industrial protein, wherein a strain of *Y. lipolytica* according to the invention is cultured on a medium providing for its growth.

The examples below will enable other characteristics and advantages of the present invention to be revealed.

Figures 1, 2, 14:
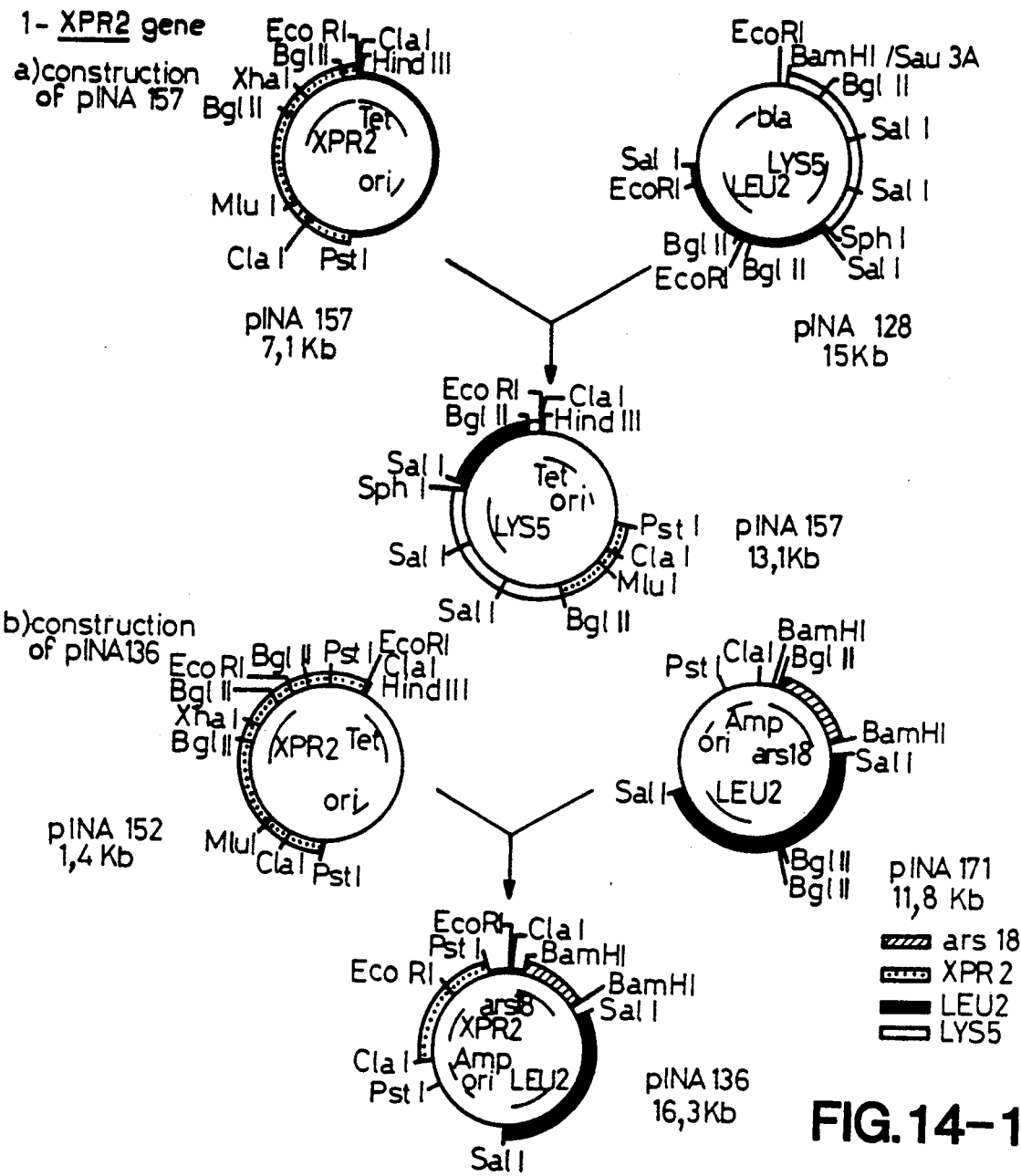

The attached figures are as follows:

FIG. 1: Diagram of transmission of an extrachromosomal plasmid showing a propensity for maternal segregation, in cells with mycelial growth or in yeast-shaped cells. The growth (G) or arrest of growth (A) is due to the presence or absence, respectively, of the plasmid (symbolized by an empty circle) which carries the selective marker gene; the nucleus is represented by the solid circle.

FIG. 2: Morphology of the colonies of the Fil+ parent strain (INAG33122) and of the Fil− mutant (INAG33129), seen from above (A) or from below (B). Magnification 5 to 10 times.

Figures 3, 14:
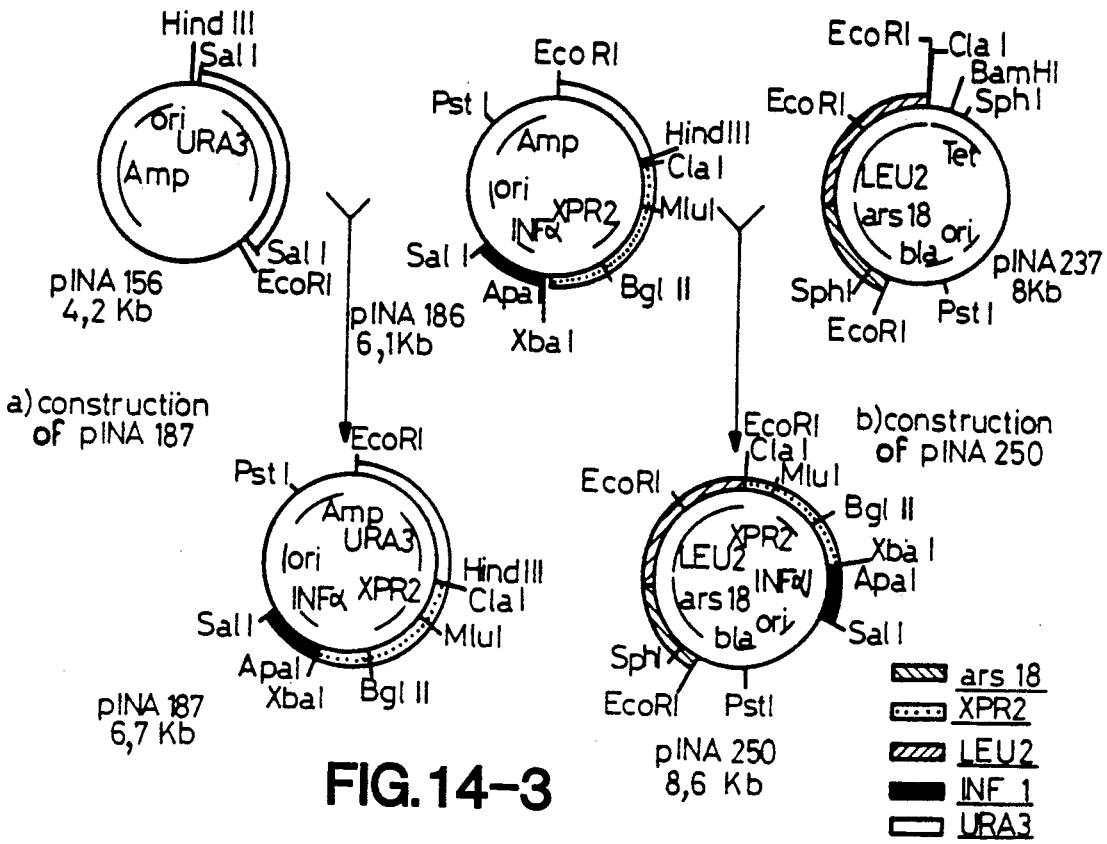
Figures 4, 14:
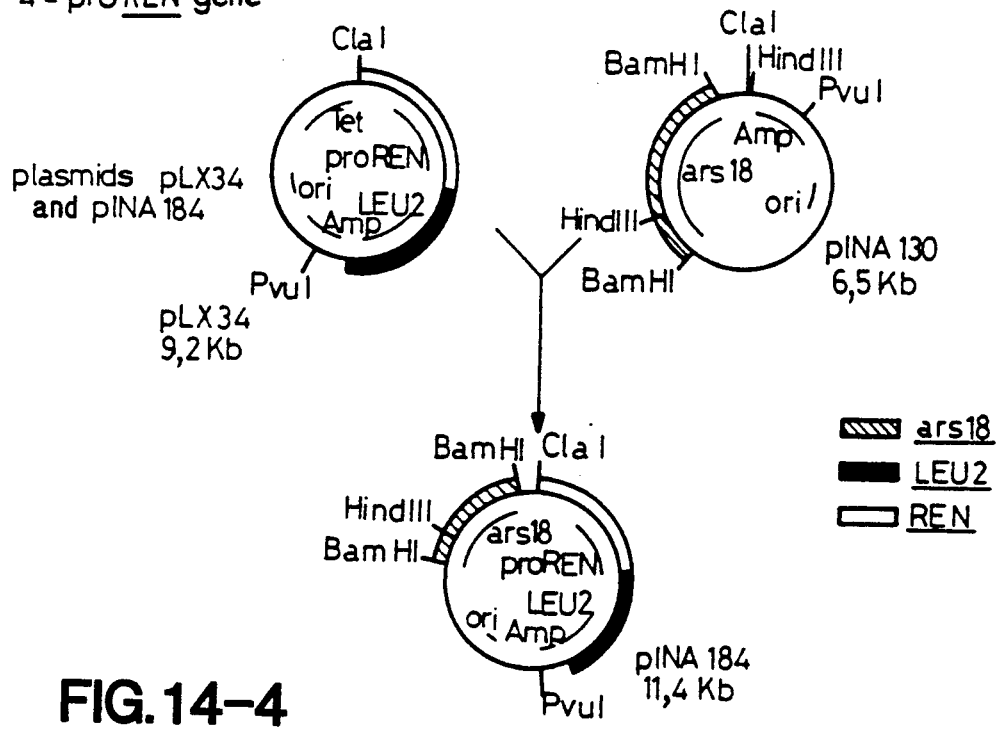

FIG. 3: Morphology of the cells of Fil+ strain (A) and of Fil− mutant (B) observed in the light microscope (magnification 400 times).

Figure 4:
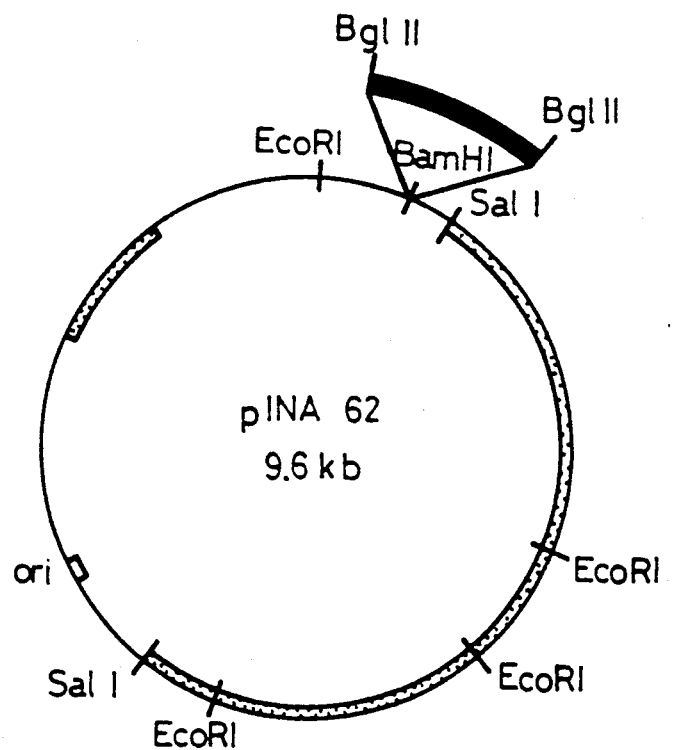

FIG. 4: Map of the integrative vector pINA62 showing the strategy for construction of the library of BglII fragments (in black) at the single BamHI site of this plasmid. The shaded region is the bla gene for resistance to ampicillin, the dotted region is the LEU2 of *Y. lipolytica* and ori represents the bacterial origin of replication of the plasmid.

Figure 5A:
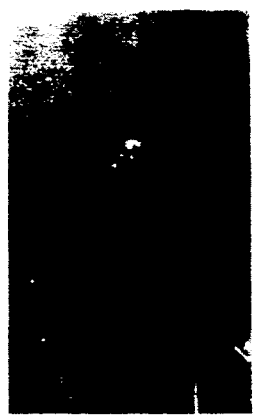
Figure 5B:
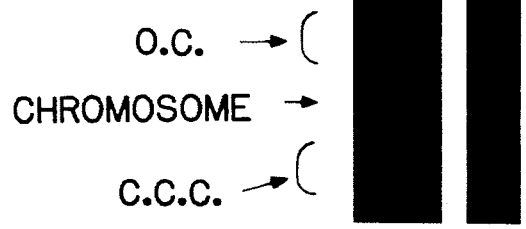

FIG. 5 (parts A and B): Detection of the plasmids in the unstable transformants. The non-restricted DNA of the Fil− receptor strain (wells A and K) and of various transformants (wells B to J) was hybridized (after migration and transfer onto Biodyne) with a radioactive probe (labeled with $^{32}P$) consisting of plasmid pINA62. Two sets of gels are shown; at the left, the transformants 2-18 (well B), 2-26 (well C), 2-39 (well D), 3-19 (well E) and 2-75 (well F) are seen; at the right, the transformants 2-18 (well G), 1-68 (well H), 1-77 (well I) and 1-27 (well J). In the name of the transformants, the first figure indicates the pool of origin and the second is a serial number. The chromosomal DNA is revealed by the LEU2 portion of the probe in the form of a diffuse band (the DNA not being restricted), and is visible in most of the wells (see, in particular, the receptor cell in which it constitutes the only signal, wells A and K). The differences in intensity reflect, in fact, the variable amounts of DNA deposited on the gel. The plasmids are present at least in open circular (OC) form, and several times also in CCC form. Study of the figure enables 5 categories of sizes of plasmids to be observed, namely, in increasing order, No. 1 (well D), No. 2 (wells B, C, F, G), No. 3 (well H), No. 4 (well E) and No. 5 (wells I and J).

Figure 6:
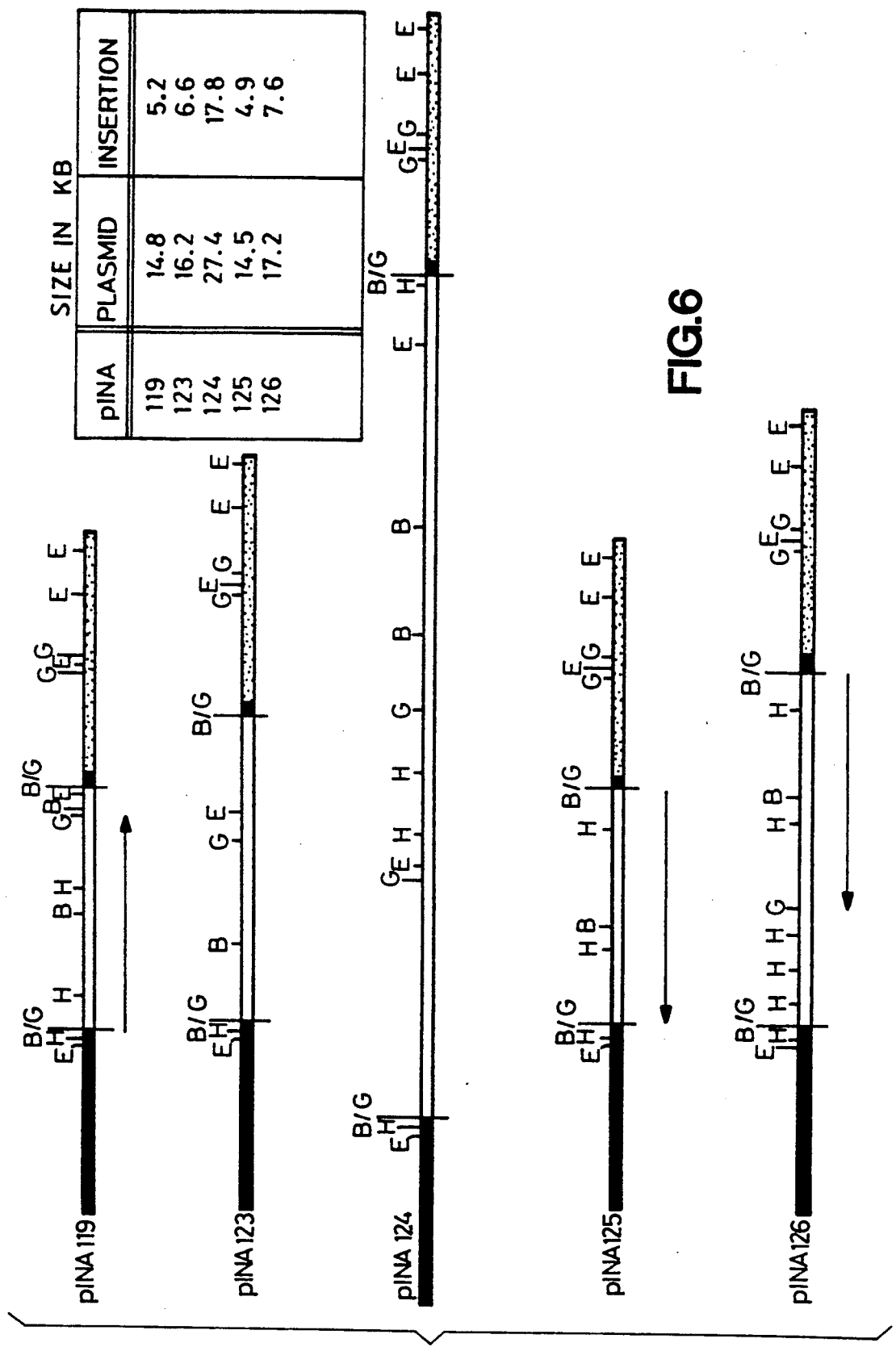

FIG. 6: Restriction map of the 5 plasmids isolated from representative transformants of the 5 categories defined in FIG. 5, namely:

pINA119 originates from the transformant 2-18 (category 2)

pINA123 originates from the transformant 1-68 (category 3)

pINA124 originates from the transformant 1-77 (category 5)

pINA125 originates from the transformant 2-39 (category 1)

pINA126 originates from the transformant 3-19 (category 4)

The pBR322 portion is represented in black, the LEU2 gene dotted and the insertion carrying the ars sequence left blank. The plasmids are shown opened at the SalI site of pBR322, but the SalI map has not been established for the insertions. The restriction sites are as follows: B=BamHI, G=BclII, E=EcoRI, H=HindIII, B/G=BamHI site destroyed by the cloning of the BclII fragment. The arrow indicates the homologous region (bounded by two BglII sites) with its orientation.

Figure 7:
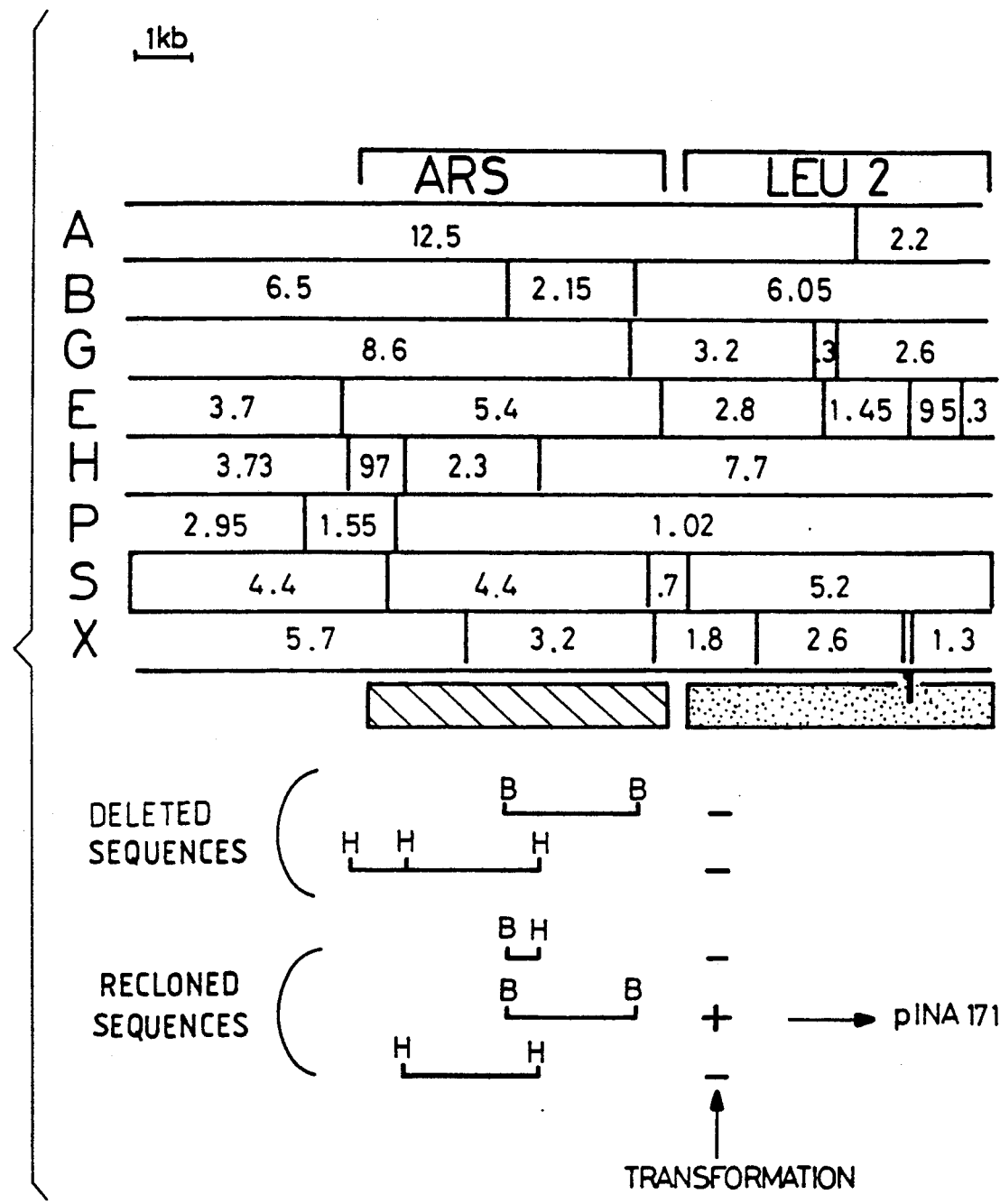

FIG. 7: Restriction map of ars plasmid pINA119. The portion carrying the ars sequence is represented shaded and that carrying LEU2 dotted. The sizes are to scale (in kilobases). The enzymes used are: A=ApaI, B=BamHI, G=BglII, E=EcoRI, H=HindIII, P=PstI, S=SalI and X=XhoI. At the bottom of the diagram, there are shown the deletions and reclonings carried out and their efficacy in high frequency transformation in *Y. lipolytica* strain leu2-35 (with non-restricted DNA). Only plasmid pINA171 containing the 2.2 kb BamHI-BamHI fragment is efficacious.

FIG. 8: Construction of a minivector for *Y. lipolytica*.

A - This 8.2 kb vector contains:

the 2.2 kb (BamHI-BamHI) ars fragment, thereby permitting its replication in *Y. lipolytica*;

the LEU2 gene (coding portion without the terminator, equivalent to 3 kb from SalI to ApaI);

the bacterial origin of replication colE1, thereby permitting its propagation in *E. coli*;

the promoters of bacteriophages T3 and T7, which enable RNAs to be made with high efficacy (and hence, for example, to synthesize very hot radioactive probes);

the M13 sequences which facilitate sequencing (the complementary primer sequences of the DNA strands on each side of the multisite are commercially available);

a multisite which permits either the subsequent cloning of genes, or the initiation of deletions in vitro, by means of exonuclease III or of the enzyme Bal31, for example.

B - Fine map of the ars fragment in its 2.2 kb BamHI-BamHI region (diagram to scale, in base pairs).

In this figure, the restriction sites are symbolized by: A=ApaI, B=BamHI, C=AccI, H=HindIII, N=NotI, R=RsaI, S=SalI, T=TagI, V=EcoRV.

FIG. 9: Expression of beta-galactosidase. Diagram of construction of plasmid pINA135 from the integrative plasmid pINA98. The cloning of the ars between the two BglII sites present on the SalI-SalI fragment of *Y. lipolytica* DNA which carries the LEU2 gene has no effect on the expression of the latter, since these sites are outside the actual coding sequence. The LEU2 promoter (Sau3a fragment cloned into BamHI, see ref. 5) is recognized upstream from the lacZ gene.

Figure 10:
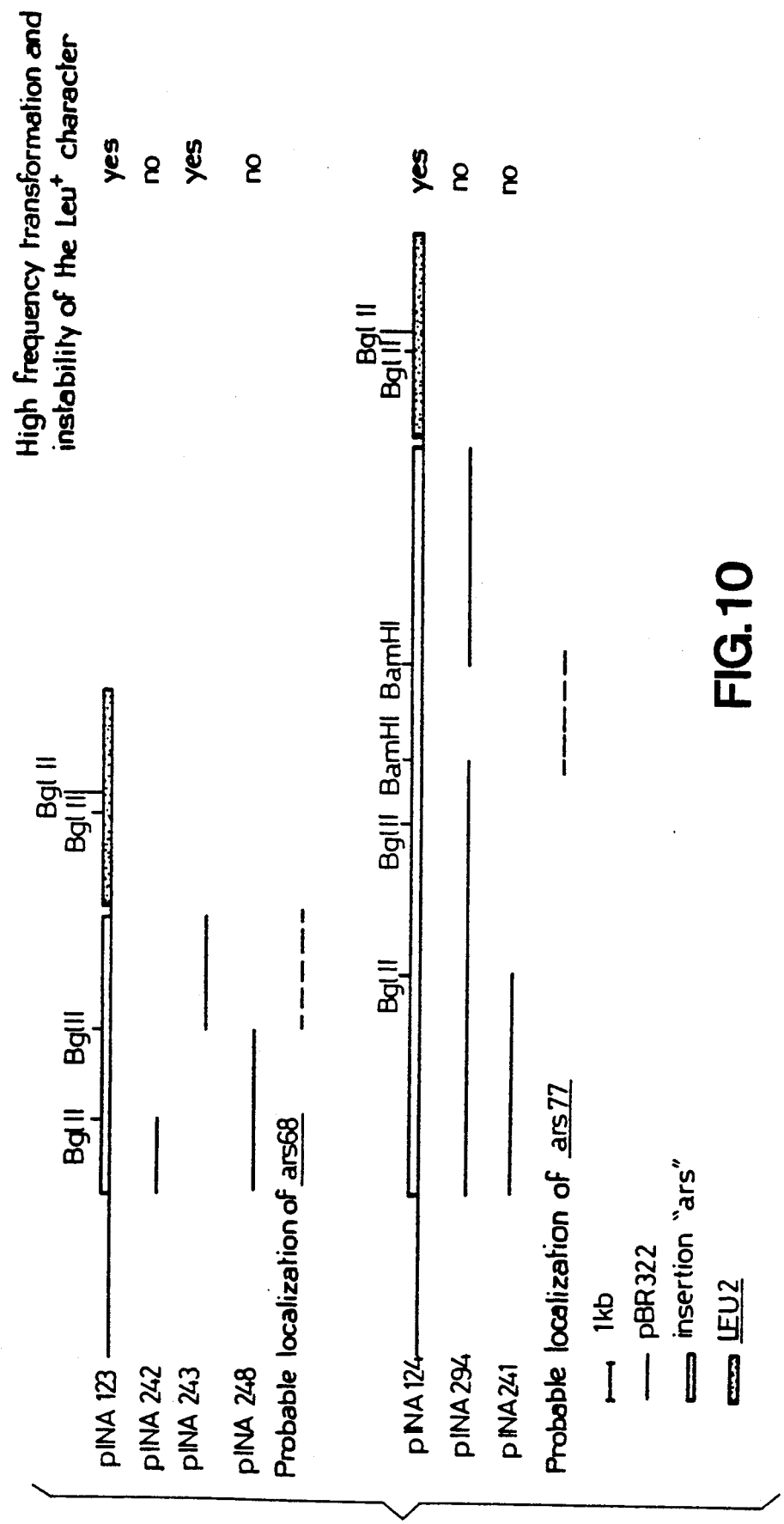

FIG. 10: Reduction of the fragments carrying ars68 and ars77. Only the portions which remain in the derived plasmids, all of which contain the LEU2 gene as a transformation marker, are shown.

Figure 11:
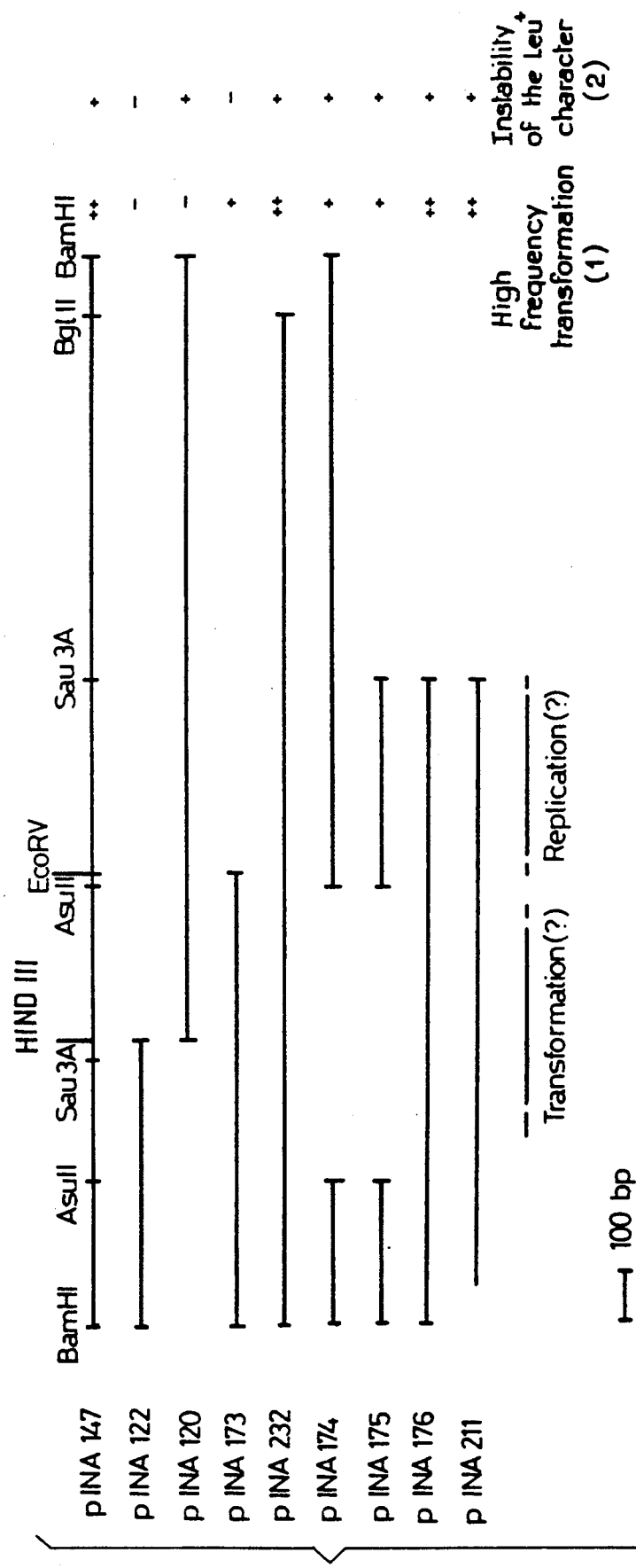

FIG. 11: Reduction of the ars18 sequence. The plasmids whose names appear at the left comprise the portion of ars18 underlined in the center, as well as the LEU2 gene of *Y. lipolytica*, and are present, depending on the case, in one or other of the bacterial vectors pBR322 (pINA122, pINA120, pINA232) or Bluescript (pINA147, pINA173, pINA174, pINA175, pINA176, pINA211). All were constructed by deletions or reclonings, using the restriction sites appearing at the top, with the exception of pINA211 whose construction is explained in the text. The two regions which appear to be essential, one for high frequency transformation and the other for the self-replicative capacity, are underlined in the center.

Notes: (1) The frequency of transformation is symbolized by ++ (more than 5,000 transformants per 1 g of DNA) or by + (200–500 transformants per 1 g of DNA), or by − (fewer than 200 transformants per 1 g of DNA).

(2) The instability of the Leu+ phenotype is designated by + (unstable) or − (stable).

Figure 12:
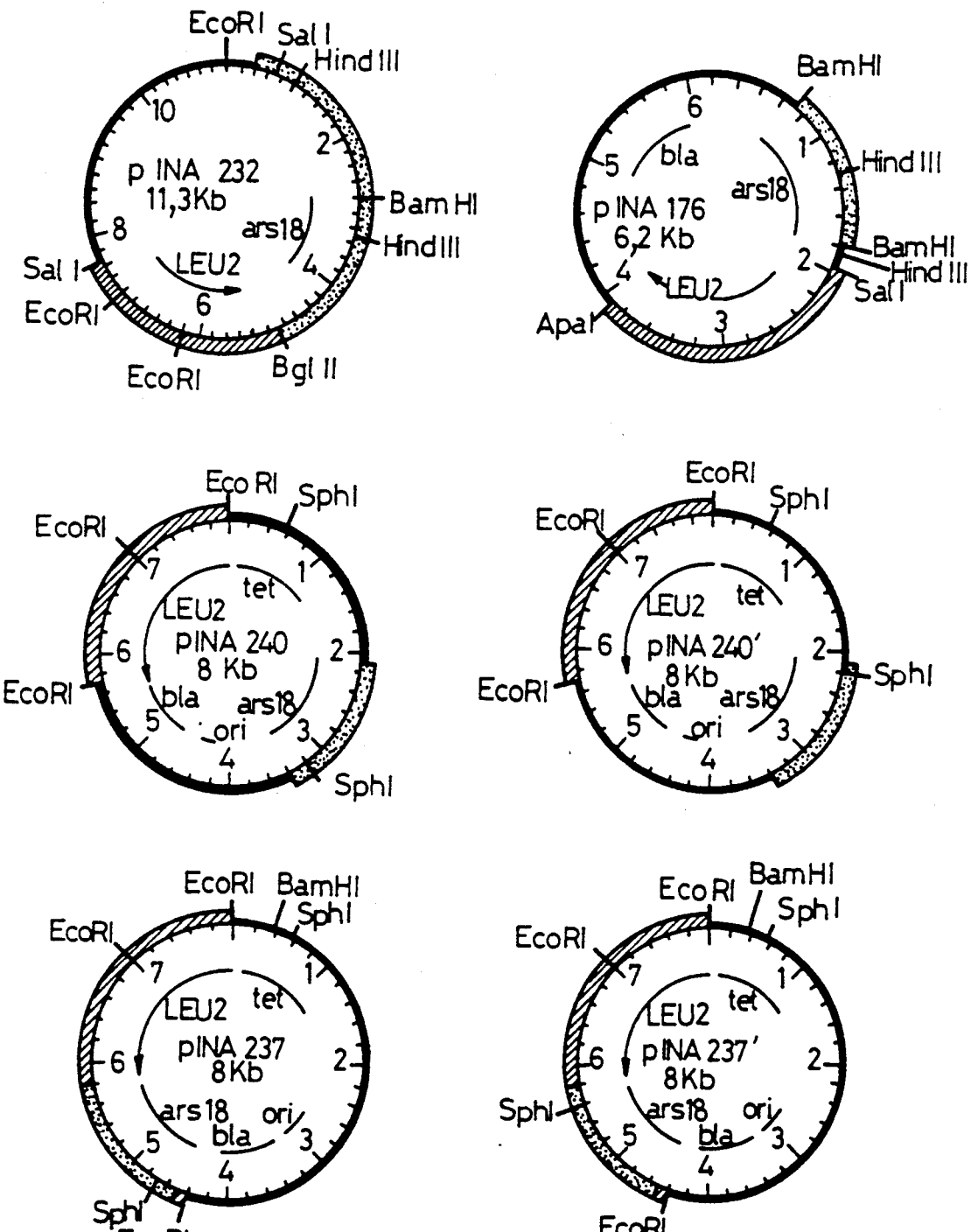

FIG. 12: Representation of various *E. coli* - *Y. lipolytica* shuttle plasmids carrying the ars18 sequence. All permit a selection for the Leu+ phenotype in yeast. Plasmid pINA232 is derived from plasmid pINA119, described in FIG. 6, by a BglII deletion; it hence carries, upstream from the single BamHI site, a region which is not necessary to the ars function. The five other plasmids possess the 1.3 kb minimal ars region defined in FIG. 11. The bacterial portion consists of Bluescript in the case of pINA176 and of pBR322 in the other plasmids. The two vectors pINA237 and pINA237' are derived from a pBR322 plasmid in which the 2298 bp fragment carrying the LEU2 gene, obtained by partial digestion of pINA62, has been inserted at the single EcoRI site; the 1.3 kb BamHI fragment carrying ars18 has then been inserted in both orientations between the two BglII sites flanking LEU2. Plasmids pINA240 and pINA240' are derived from a pBR322 plasmid in which a BglII linker (Boehringer reference 909734), which has enabled the BamHI fragment carrying ars18 to be introduced in both orientations, has been inserted at the single PvuII site. The LEU2 gene has been introduced as above into the resulting plasmids.

FIG. 13: Sequence of ars18. The restriction sites referred to in FIG. 11 are noted above the sequence. The direct repeats (A to G) and reverse repeats (H to M) comprising at least 10 bases are underlined, and the number of bases is indicated after a dash. Note that the repeat K is included in D and that the sequence E is itself a palindrome. The remarkable direct repeat A-B-C (1075-1121 and 1147-1183) is also noted. Moreover, AT alternations are found (regions 500-520 and 1220-1250), as well as repetitions of A (region 150-180) or of T (region 340-370). Finally, the boxed sequences correspond to imperfect homologies with the ars consensus defined in S. cerevisiae yeast (9 or 10 homologous bases out of the 11 contained by the consensus WTTTATPTTTW, where W denotes A or T and P denotes A or G; see ref. 26).

FIG. 14 parts 1-4: Construction of the integrative and replicative plasmids used for the gene amplification.

1) XPR2 Gene a) pINA157—this disruption vector was produced by replacement of the internal BglII fragment (0.9 kb) of the XPR2 gene by a BglII fragment (6.9 kb) of pINA128 (ref. 14) carrying the LYS5 gene;
b) pINA136—this replicative vector was produced by the insertion of a ClaI fragment (4.5 kb) of pINA152 containing the XPR2 gene into the replicative vector pINA171 containing ars18 and the selection marker LEU2.

2) SUC2 Gene a) pINA169—integrative vector containing the SUC2 gene under the control of the XPR2 promoter (FIG. 17) and the LEU2 marker. The vector is integrated at the XPR2 site into strain JM55;
b) pINA181—replicative vector containing the SUC2 gene, in the form of a 3.9 kb ClaI-SalI fragment of pINA169 inserted between the ClaI and SalI sites of the replicative vector pINA176 (FIG. 12).

3) Pro-INF-alpha$_1$ Gene a) pINA187—integrative vector containing the pro-INF-alpha$_1$ gene of pINA186 (FIG. 19) and the Y. lipolytica URA3 marker originating from pINA156. The vector is integrated at the XPR2 site into strain JM77;
b) pINA250—replicative vector containing the pro-INF-alpha$_1$ gene constructed by ligation of the ClaI-PstI fragment (4.2 kb) of pINA186 with the ClaI-PstI fragment (4.4 kb) of the replicative vector pINA237 (FIG. 12).

4) ProREN Gene a) pLX34—integrative vector containing the gene coding for bovine prorennin (ref. 20);
b) pINA184—replicative vector containing the proREN gene. The ClaI-PvuI fragment (5.5 kb) of pLX34 carrying both the proREN gene and the LEU2 marker was ligated with the ClaI-PvuI fragment (5.9 kb) of pINA130 containing ars18, thereby re-forming the marker gene for resistance to ampicillin.

Figure 15:
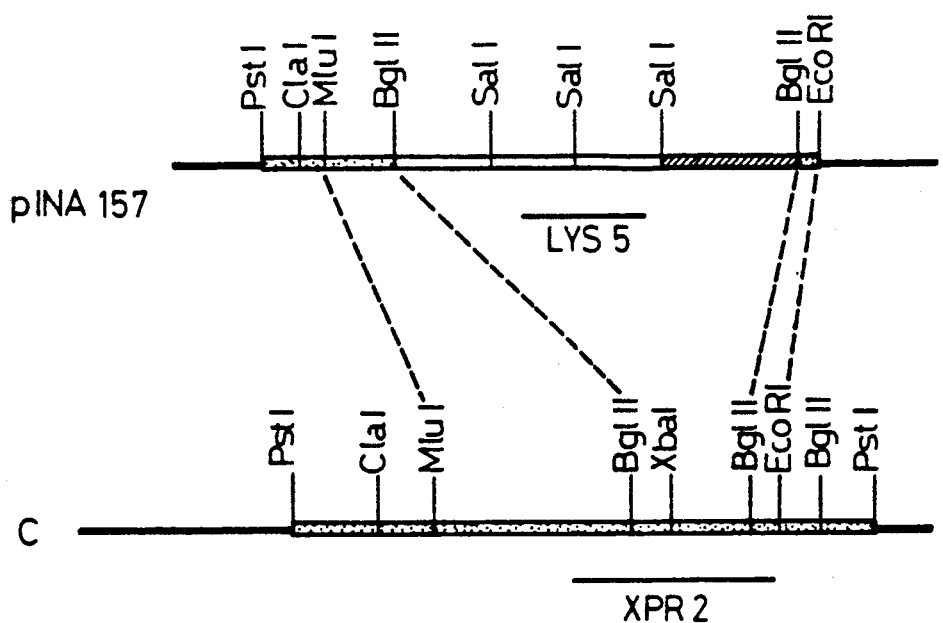

FIG. 15: Diagrammatic representation of the construction of strain JM23. The chromosomal restriction map of the XPR2 locus (C) of strain JM12, as well as the restriction map of the disruption plasmid pINA157, are shown. The disruption plasmid has been restricted beforehand with the restriction enzymes MluI annd EcoRI. Replacement of the XPR2 gene by the LYS5 gene has been obtained by double "crossing over" in the MluI-BglII and BglII-EcoRI regions of homology.

Figure 16:
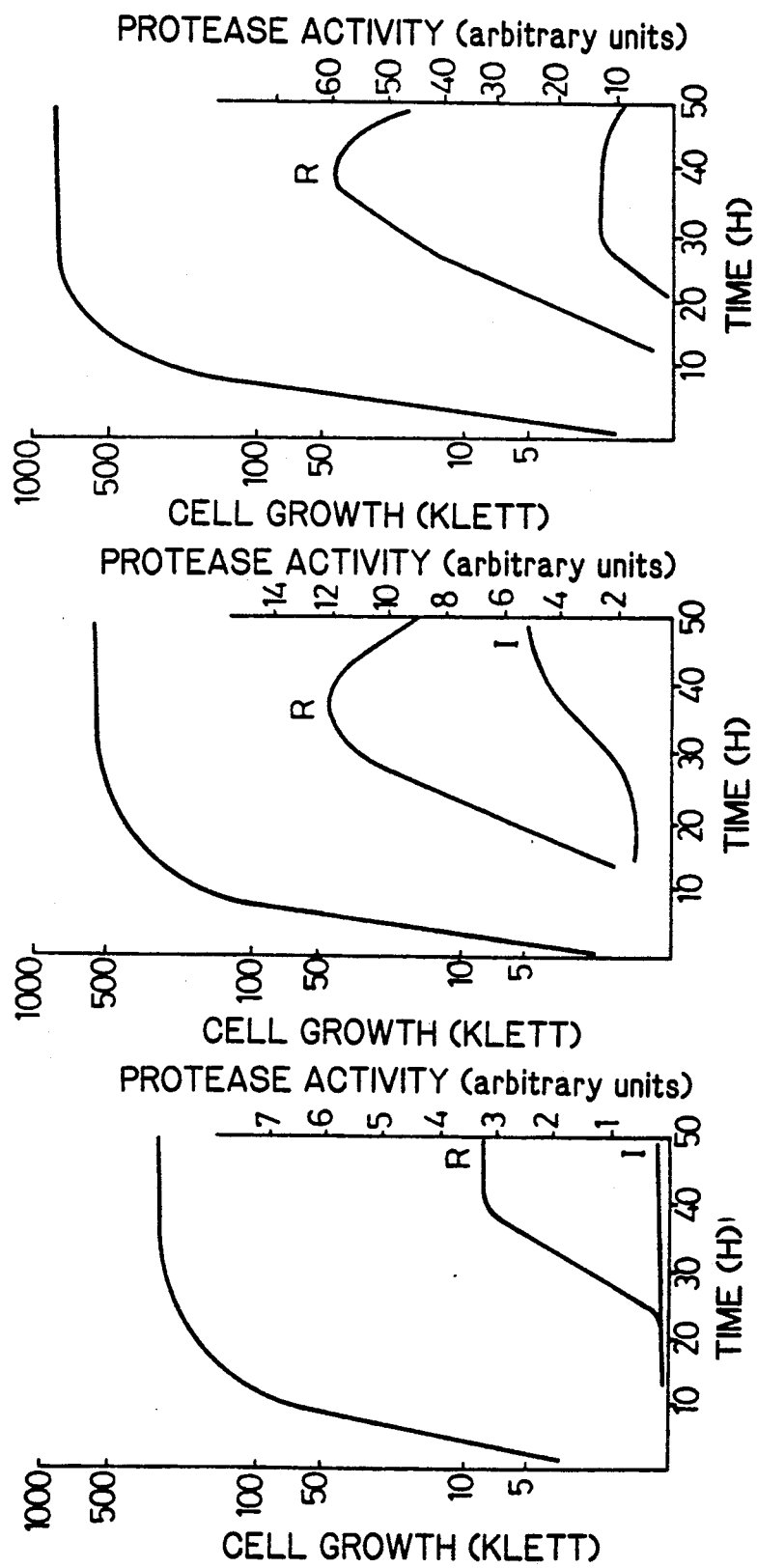

FIG. 16 (parts A-C): Comparison of the production of protease activity produced during growth by strain JM12 possessing the integrated XPR2 gene (I) and strain JM70 possessing the XPR2 gene on the replicative vector pINA136 (R), cultured at 28° C. in YNB (A), YNBpp (B) and YPDm (C) media. The protease activity is expressed in arbitrary units.

Figure 17:
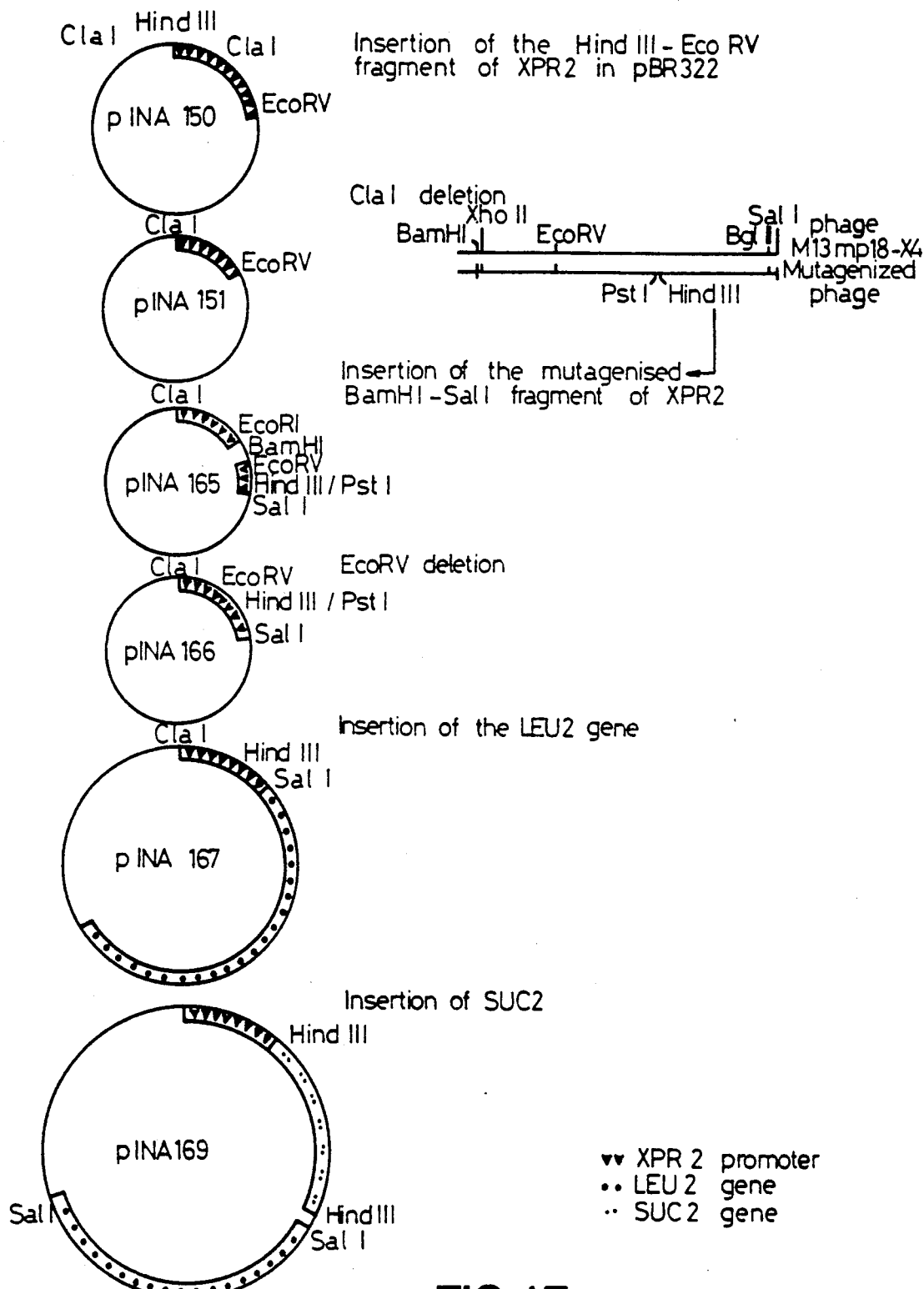

FIG. 17: Diagram of construction of plasmid pINA169 carrying the pre-XPR2-SUC2 fusion. The upstream region of the XPR2 promoter carried by a HindIII-EcoRV fragment has been inserted into pBR322 (pINA150). A ClaI deletion then permits removal of the HindIII site (pINA151). Furthermore, a HindIII site has been created after the region coding for the signal sequence of the protease, by directed mutagenesis. To this end, the phage M13mp18-X4 carrying a 553 bp XhoI-BglII fragment covering the region around the ATG has been mutagenized using the mutagenic oligonucleotide:

(5'CAGCATCAGAAGCTTCT-
GCAGGGGCG3').

The mutagenized fragment, purified after a BamHI-SalI restriction, has been introduced into pINA151 to create plasmid pINA165. By an EcoRV deletion, plasmid pINA166, which possesses the XPR2 promoter and the LEU2 sequence (5.3 kb fragment of pINA62) in pINA166, has been generated. Finally, the SUC2 gene of S. cerevisiae, originating from a 2 kb HindIII fragment of pRB58 (ref. 18), has been inserted to create the final plasmid pINA169.

Figure 18A:
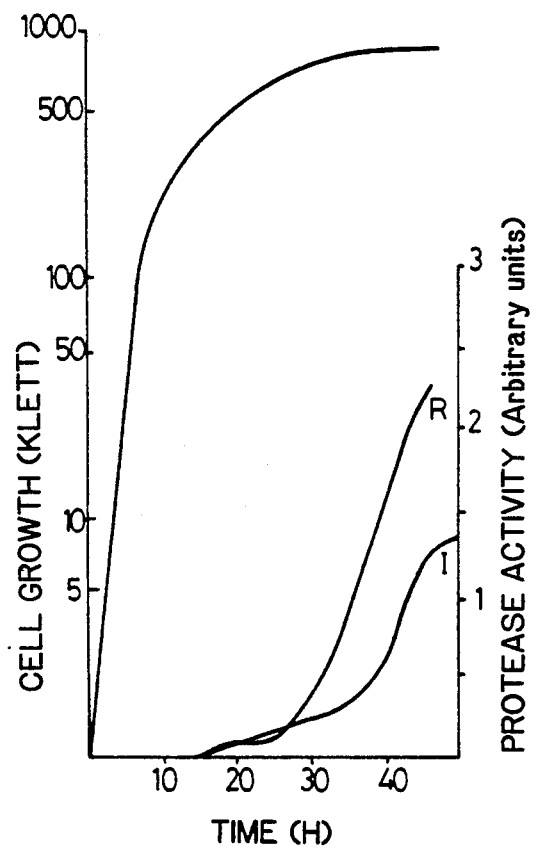
Figure 18B:
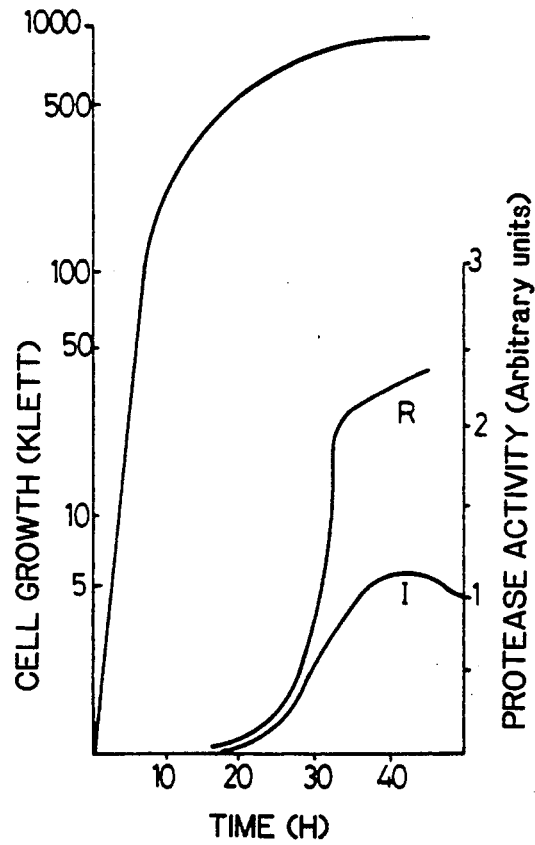

FIG. 18 (parts A and B): Comparison of the production of invertase activity during growth by strain JM58 possessing the integrated SUC2 gene (I) and by strain P1 possessing the SUC2 gene on the replicative vector pINA181 (R), at 28° C. in YPDm sucrose and YPDm glucose (B) medium.

Figure 19:
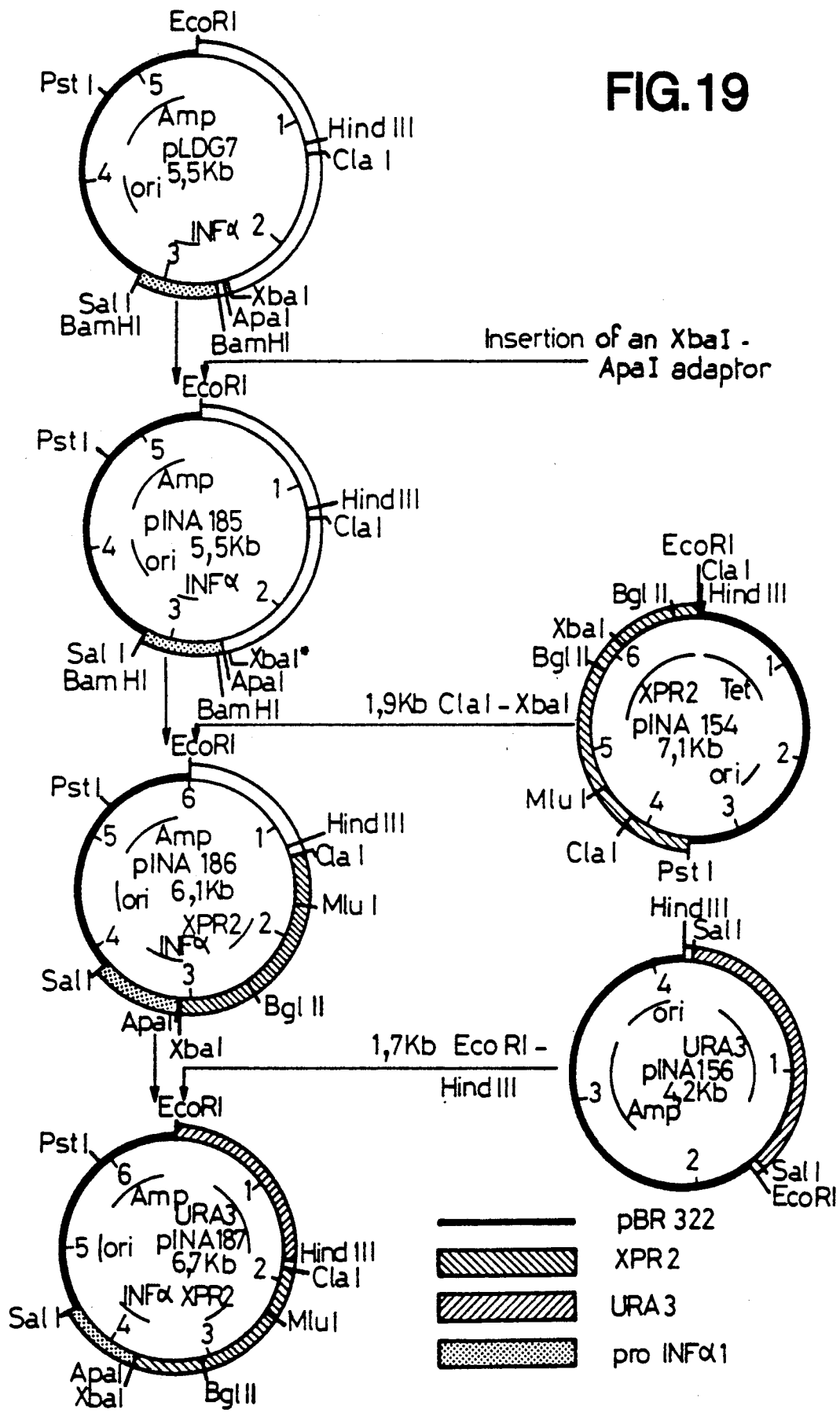

FIG. 19: Diagram of construction of plasmid pINA187 carrying the preproXPR2-IFN-alpha1 fusion. The vector pLD67 containing the pro-IFN-alpha1 gene coding for porcine interferon-alpha$_1$ has been described by La Bonnardière and Lefèvre (ref. 19). It has been opened with the enzymes XbaI and ApaI then ligated with the oligonucleotides A (56-mer) and B (48-mer). The latter enable an XbaI-AcaI adaptor to be formed, creating in phase with the "prepro" region of the protease a Lys-Arg site (underlined below), followed by the coding sequence for mature interferon (pINA185).

A:
CTAGATCTAAGCGATGTGACCTGCC-
CCAGACCCACTCCCTGGCCCACA
CCAGGGCC

B:
TAGATTCGTTACACT-
GGACGGGGTCTGGGTGAGG-
GACCGGGTGTGGTC

The hybrid gene is produced by the insertion of 1.9 kb ClaI-XbaI fragment which re-forms the XPR2 promoter and the coding sequence for the prepro portion of the AEP followed by the coding sequence for interferon (pINA186). The integrative vector pINA187 possesses the URA3 selection marker carried by a 1.7 kb EcoRI-HindIII fragment originating from pINA156.

EXAMPLE 1

Isolation of Mutants

The formation of mycelium on the microscopic scale results in a different morphology of the colonies at the macroscopic level, namely so-called "fuzzy" or rough colonies, forming skins and surrounded by tufts at the surface of the agar (FIG. 2). This morphology is more distinct when the cells are not too numerous per dish (fewer than 100) and when they are on a rich medium with a high glucose concentration.

In practice, a culture of the strain INAG33122 (MatB, leu2-35, xpr2, lys2-5, ade1) is irradiated with UV rays, at a dose permitting 60% survival. After a phase of expression in complete medium, the cells are plated (approximately 500/dish) on $YPD_{30}$ medium (yeast extract 1%, peptone 1%, glucose 30 g/l, agar 20 g/l) or $YPD_{10}$ medium (with only 10 g/l of glucose). After 8 days' incubation at 28° C., the colonies showing an atypical morphology are identified with a binocular magnifier and then purified. Their phenotype is confirmed by plating at low colony density and microscopic observation (FIG. 3). Finally, 7 mutants are selected out of the 61,000 initial colonies (frequency $1.1 \times 10^{-4}$), and only one possesses a phenotype which is sufficiently distinct and stable for the subsequent experiments. This phenotype is referred to as Fil− and the genotype is designated fil-18. The strain bears the name INAG33129 (MatB, leu2-35, xpr2, lys2-5, ade1, fil-18).

EXAMPLE 2

Construction of the Library

Since the receptor strain possesses the (very stable) leu2-35 mutation (originating from the strain DX465-7B of D. M. Ogrydziak, described in the patent cited as reference 8), a library is constructed in plasmid pINA62 (ref. 5) which contains the LEU2 allele cloned at the SalI site of pBR322 (FIG. 4). The DNA of Y. lipolytica strain 15901-4 (MatB, ura2-21, lyc1-5, LYS1-5) was digested completely with the enzyme BglII and mixed with plasmid pINA62, cut beforehand with BamHI and dephosphorylated with alkaline phosphatase. The library does not completely cover the genome, and consists of 4 sets (or "pools") representing a total of 7,000 clones, 89% of which are referred to as hybrids (that is to say, contain a cloned fragment). The average size of the insertions, estimated on some twenty plasmids taken at random, is in the region of 5.2 kb. The DNA of these pools was extracted and purified on a cesium chloride gradient with ethidium bromide.

EXAMPLE 3

Selection of the Ars Sequences

Still on the basis of the hypothesis according to which ars sequences should be relatively unstable in Y. lipolytica, the strain INAG33129 is first transformed with the DNA of the pools and unstable clones are then sought among them. The DNA of the pools was not restricted beforehand, so as to permit a direct selection of extrachromosomally replicating sequences; it is, however, verified on a small sample that this DNA, cut partially or completely with the enzyme ApaI (single site in the starting plasmid pINA62 and situated in the LEU2 sequence), is capable of transforming by integration, like pINA62 (even if at a lower frequency than the latter). The numbers of transformants are shown in Table I, together with the number of clones tested and the percentage of unstable clones (which is in the region of 10%).

TABLE I

| | | Efficacy of the different pools of DNA of the library for the transformation of Y. lipolytica and for the production of unstable clones | | | | |
|---|---|---|---|---|---|---|
| | | Efficacy of transformation (Tr/1 g of DNA) | | No. of clones (obtained with uncut DNA) | | |
| Pool No. | Pool size (1) | DNA cut with ApaI | Uncut DNA | tested for stability | No. of unstable clones | % of unstable clones |
| 1 | 2500 | 3700 | 15 | 85 | 10 | 12 |
| 2 | 2500 | 1500 | 300 | 16 | 12 | 16 |
| 3 | 1000 | 10500 | 70 | 44 | 1 | 2 |
| 4 | 1000 | N.T. | 10 | 13 | 0 | ≤8 |
| | | | total | 218 | 23 | 11 |

(1) Number of bacterial clones

To test the instability of the transformant clones, the latter are streaked on rich medium and, after growth, are replicated on the minimum medium (Yeast Nitrogen Base without ammonium sulfate 1.7 g/l, lysine nitrogen source 1 g/l, adenine HCl 100 mg/l, glucose 10 g/l, agar 20 g/l) and minimum medium supplemented with L-leucine (200 mg/l). The unstable clones are those which have segregated significantly from the Leu− colonies.

EXAMPLE 4

Characterization of the Ars Plasmids

The unstable colonies are maintained on selective medium, and their total DNA is extracted by a minilysate method which has already been described (9). This DNA underwent an agarose gel electrophoresis and was then transferred onto a nylon membrane (Biodyne, Pall France) by Southern's (10) method and hybridized with the DNA of plasmid pINA62, labeled with $^{32}P$ by the nick translation technique (Nick-Translation Kit, Amersham France).

This radioactive probe enables the chromosomal LEU2 allele to be identified in the form of a very diffuse band, the DNA not being restricted, and an extrachromosal band corresponding to the transformant plasmid (pINA62+insertion). From the differences in migration of the plasmid bands (FIG. 5), which often correspond, moreover, to closed circular forms (referred to as CCC, standing for "covalent closed circular"), it can be seen that there are at least 5 sizes of plasmids. The additional bands which are seen in some wells might correspond either to the existence of several plasmids in the same strain, or to open circular (OC) forms of the same molecule. To distinguish between the two hypotheses, E. coli strain HB101 (hsdR−, hsdM−, recA13, supE44, lacZ4, leuB6, proA2, thi-1, Sm$^R$) is transformed with the DNA extracted from the transformants, selecting colonies resistant to ampicillin (the bacterial gene for resistance being present on pINA62). For each of the yeast transformants selected, E. coli colonies are obtained, from which the plasmid is extracted and analyzed with restriction enzymes. Each yeast transformant proves to contain only a single type of plasmid. The restriction maps of the 5 plasmids selected are shown in FIG. 6. The analysis of these maps, as well as the results of hybridization (data not described in the present patent) carried out between restrictions of these plasmids and one of the ars sequences (a fragment of plasmid pINA119), show that 3 of the cloned ars fragments are, in fact, homologous. The fragments in question comprise the same 4.5 kb BglII-BglII fragment, to which other fragments are, where relevant (in the case of pINA119 and pINA126) joined during the ligation. In conclusion, 3 different ars sequences are available, carried by plasmids pINA119, pINA123 and pINA124 and localized on 5.2 kb, 6.6 kb and 17.8 kb DNA fragments, respectively.

EXAMPLE 5

Transformation of Y. Lipolytica with the Cloned Sequences

To show that the plasmids which have been selected as extrachromosal molecules in Y. lipolytica are capable of transforming this yeast at high frequency, the Fil− mutant strain (INAG33129) and also the Fil+ strain (INAG33122) are used. Both prove to be transformable at high frequency by pINA119 (Table II, experiments 1 and 2). It may be seen from these results that the optimum transformation of the strain INAG33129 by integration (in this case, plasmids pINA62 or pINA119 restricted with ApaI) does not correspond to the optimum replicative transformation obtained with non-restricted pINA119 (compare experiment 3 for the former case with experiments 1 and 2 for the latter). The biological factors determining this optimum are still unknown, which explains the very marked quantitative fluctuation of the results from one experiment to another. However, this fluctuation does not call into question the fact that the plasmid pINA119 always transforms from 20 to 100 times as much as the intact starting plasmid pINA62, which testifies well to the presence of the ars.

In experiment No. 3, plasmids pINA125 and pINA126, which prove to carry a common fragment with pINA119, transform the strain INAG33129 at almost the same frequency (pINA125, which is a little smaller, transforms better). pINA123 and pINA124 may be considered to be almost as efficacious, all the more so since pINA124 is almost double the size of pINA119.

Moreover, the data of Table II collectively show that the Fil+ strain is also transformable by the ars plasmids, although at lower frequency than the Fil− mutant in this experiment. These plasmids transform the strain INAG33122 at least 100 times as well as non-restricted pINA62. This result appears very surprising in the light of the initial hypothesis calling into question the mode of cell division in the selection of the ars sequences. It is hence necessary to find out whether an ars plasmid is also maintained extrachromosomally in the Fil+ strain. A hybridization experiment after Southern transfer, similar to that described in Example 4, shows that this is indeed the case in Fil+ transformants obtained with pINA119 (data not shown). To characterize this unexpected situation further, the stability of the transformants is studied.

EXAMPLE 6

Stability of Ars Sequences

The stability of the 5 plasmids pINA119 and pINA123 to pINA126 is estimated after 5 to 10 generations in selective liquid medium (without leucin) and parallel plating on minimum medium and medium supplemented with leucin. The ratio of the number of colonies counted on each medium gives the percentage of prototrophs as shown in Table IIIA. This percentage varies from 65% to 84%, and there is no statistically significant difference between the stabilities of the different ars sequences in the strain INAG33129. In contrast, it is noteworthy that this percentage is so high, in distinction to the behavior of ars sequences in S. cerevisiae (2).

To study this stability in detail, special attention is directed towards the ars sequence present on pINA119. Transformants obtained either in the Fil− strain (INAG33129) or in the Fil+ strain (INAG33122) are cultured for approximately 10 generations in selective and non-selective media, and the percentage of auxotrophs is estimated as above, in each case. The results in Table IIIB confirm the relative stability of the ars in selective medium in INAG33129, but appear to indicate a still greater stability in the Fil+ strain. To confirm this result, a leu2-35 strain in which the mycelial growth phenotype is still more pronounced (referred to as a Fil++ strain) is transformed and a very high, or even absolute, stability is confirmed in this strain. It is verified (data not shown) that the DNA of pINA119 is always visible as an extrachromosomal band on hybridization. The stability in non-selective medium, although lower than in selective medium in each case, also follows the same progression as a function of the Fil−/Fil+ phenotype.

TABLE II

Efficacies of transformation of various plasmids on both Fil+ and Fil− strains, expressed as the number of transformants per 1 g of DNA

| Experiment | Strain | Phenotype | pINA62 NR | pINA62 R | pINA119 NR | pINA119 R | pINA171 NR | pINA123 NR | pINA124 NR | pINA125 NR | pINA126 NR |
|---|---|---|---|---|---|---|---|---|---|---|---|
| 1 | INAG33129 | Fil− | NT | 20000 | 15000 | 16000 | NT | NT | NT | NT | NT |
| 2 | INAG33129 | Fil− | NT | 8900 | 47000 | 15000 | NT | NT | NT | NT | NT |
|  | INAG33122 | Fil− | NT | 80000 | 55000 | 25000 |  |  |  |  |  |

TABLE II-continued

Efficacies of transformation of various plasmids on both Fil+ and Fil— strains,- expressed as the number of transformants per 1 g of DNA

| | | | DNA | | | | | | | | |
|---|---|---|---|---|---|---|---|---|---|---|---|
| | | | pINA62 | | pINA119 | | pINA171 | pINA123 | pINA124 | pINA125 | pINA126 |
| Experiment | Strain | Phenotype | NR | R | NR | R | NR | NR | NR | NR | NR |
| 3 | INAG33129 | Fil— | 800 | 88000 | 6000 | NT | 33000 | 6900 | 2100 | 15000 | 6100 |
| | INAG33122 | Fil+ | 0 | 12000 | 600 | NT | 1000 | 250 | 375 | 750 | 500 |

NR: Non-restricted
R: Restricted with ApaI
NT: Not determined

TABLE III

A) Stability after 5 generations in selective medium in the strain INAG33129 (Fil—)

| DNA | pINA119 | pINA123 | pINA124 | pINA125 | pINA126 |
|---|---|---|---|---|---|
| % prototrophs | 65 | 72 | 84 | 79 | 69 |

B) Stability of plasmid pINA119 after 10 generations on various media and in several strains

| | | % of prototrophs on | |
|---|---|---|---|
| Strain | Phenotype | selective medium | non-selective medium |
| INAG33129 | Fil— | 60–70 | 10–15 |
| INAG33122 | Fil+ | 70–80 | 60 |
| ML11 | Fil++ | 85–100 | 80–90 |

It is hence thought that, in distinction to the initial hypothesis, the failure in the isolation of the ars sequences is not due to an excessively great instability of these sequences which would prevent their propagation in the mycelia, but rather to the fact that they could never be found by looking for unstable clones. In effect, in the Fil+ strains, these sequences appear to be as stable as integrations.

Under these conditions, it is necessary to demonstrate that the plasmids always remain extrachromosomal and that the stability is not due to the existence of an integrated copy. To this end, 30 transformants of INAG33122 and 30 transformants of INAG33129 are cultured for 50 generations on selective medium, so see whether a change in the stability of these clones is found. The detailed protocol for the experiment is provided in the diagram below and in Table IV:

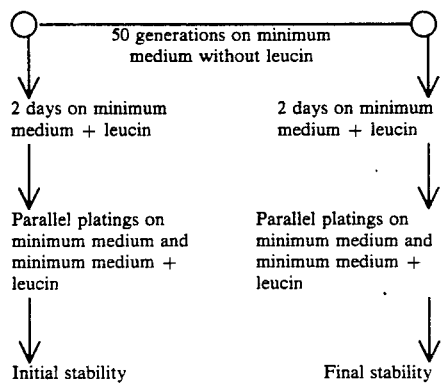

TABLE IV

Effect of a passage in selective medium for 50 generations on the stability (The results are expressed as the number of clones falling into a given category of segregation (% of prototrophs)). The experiment involves 30 clones of the Fil+ strain and 30 clones of the Fil— strain.

| | | % of prototrophs | | |
|---|---|---|---|---|
| Strain | Stability | <40% | 40–60% | >60% |
| Fil+ | initial | 0 | 11 | 19 |
| | final | 5 | 13 | 12 |
| Fil— | initial | 4 | 18 | 8 |
| | final | 12 | 11 | 7 |

The qualitative estimate as a percentage of prototrophs obtained by a passage of two days in non-selective medium, either before or after the 50 generations, shows (Table IV) that there is no translation towards a more stable profile, in the case of either the Fil+ strain or the Fil— strain. To demonstrate the absence of integration, the DNA is extracted from Fil+ and Fil— transformants before and after they have undergone the 50 generations, and restricted with the enzymes ApaI and BamHI. The restricted and non-restricted DNAs are transferred onto Biodyne after migration on agarose gel (0.7% with respect to 89 mM Tris buffer, 89 mM boric acid, 2.5 mM EDTA, pH 8.3) and hybridized with a pBR322 radioactive probe. The result (not shown) clearly demonstrates the presence of plasmid bands and the absence of bands due to an integration.

EXAMPLE 8

Fine Analysis of the Insertion Present in pINA119

It is known that, in S. cerevisiae, some ars sequences are repeated in the genome (especially those which are present close to telomeric ends), whereas others are present in a single copy (1,2,11). The situation is studied in relation to the ars sequence of pINA119. To this end, a 4.6 kb PstI-EcoRI internal fragment (FIG. 7) which covers virtually the whole of the insertion is purified and used as a probe against restriction transfers of plasmid and genomic DNA which has migrated in parallel on agarose gel. The results, analyzed in the light of the restriction map of pINA119 already shown in FIG. 6 (see also FIG. 7), show that the sequence is probably unique (barring an exact repeat in tandem of a BglII-BglII fragment). The 2.2 kb BamHI internal band reappears at the same position in the genome, like the 2.3 kb HindIII internal band. The BglII fragment revealed in the genome by the probe corresponds well to a single 4.5 kb band which is identical to the cloned fragment carried by the ars in pINA119 (in fact, in pINA119, there are two BglII fragments which have been associated during the ligation; the fragment in question here is the larger of the two, which is homologous with the insertions of pINA125 and pINA126).

Since this size is definitely (by comparison with the ars sequences described in *S. cerevisiae* (1,2,11)) larger by a wide margin than that of the minimal sequence required for the ars function, deletion and recloning experiments are performed in order to localize the ars more precisely in the insertion of pINA119. The strategy followed is depicted in FIG. 7, whence it may be concluded that the ars must be carried by the 2.2 kb BamHI-BamHI internal fragment which is present in pINA171. This plasmid is capable of transforming at high frequency both the Fil+ and the Fil− strain (Table II). It is capable of being maintained therein extrachromosomally (data not shown) and its stability therein is similar to that of pINA119 (approximately 65% of prototrophs after 5 generations in selective medium in the strain INAG33129 and 81% in INAG33122). This plasmid was used as a basis for subsequent constructions for the purpose of gene amplification.

Moreover, the BamHI-BamHI fragment was recloned into a "Bluescript M13" vector, which is a hybrid between phage M13 and the colE1 type bacterial plasmid. This vector carries a cloning multisite which made it possible, on the one hand to insert the ars at the BamHI site, and on the other hand the LEU2 3 kb minimal coding sequence included between a SalI site and an ApaI site (which was cloned between XhoI and ApaI of the multisite). This 8.2 kb vector is capable of transforming *Y. lipolytica* INAG33129 at high frequency, and was used as a basis for a further series of deletions and reclonings linked to the establishment of a fine map of the ars depicted in FIG. 8.

EXAMPLE 9

Gene Expression and Amplification by Means of the Ars Sequence

In order to demonstrate the usefulness of the ars present on pINA119 for gene amplification, the following plasmid construction is carried out: since the lacZ gene of *E. coli* coding for beta-galactosidase can be expressed in *Y. lipolytica* under the control of the LEU2 promoter (5), the 2.2 kb BamHI-BamHI ars fragment is cloned into a BglII site which is present on pINA98 (FIG. 9), an integrative plasmid carrying LEU2 and the construction for the expression of lacZ. The new plasmid pINA135 is hence replicative and is introduced into INAG33122 and INAG33129.

The expression of beta-galactosidase is identified first on a dish of minimum medium containing the chromogenic substrate X-gal. After exposure to toluene for one minute, the dishes are incubated at 37° C. and the intensity of the coloration developed by the replicative transformants is observed to be clearly greater than that of the single-copy transformant. To quantify this effect, crude extracts of the transformants are made, and the beta-galactosidase activity is assayed according to Miller's (12) protocol and referred to the quantity of proteins estimated according to Bradford's (13) method. This specific activity of beta-galactosidase is corrected by the percentage of prototrophic cells in the culture at the time at which the cells are ground. This percentage is estimated by parallel platings in selective and non-selective media. The activity results shown in Table V demonstrate that the amplification obtained with the ars varies by a factor of 2 to 9, and is similar in the Fil+ and Fil− strains.

TABLE V

| Strain | Plasmid | Cell density | Specific activity | % of proto-trophs | Corrected specific activity | Amplification |
|---|---|---|---|---|---|---|
| Fil+ | pINA171 | $2.3 \times 10^7$ | 1.6 | 81 | 1.6 | 0 |
| Fil− | pINA171 | $5.0 \times 10^6$ | 43 | 64 | 43 | 0 |
| Fil+ | pINA98 | $3.7 \times 10^7$ | 218 | 100 | 218 | |
| | | $1.5 \times 10^7$ | 562 | 100 | 562 | 390 | 1 |
| Fil+ | pINA135 | $5.1 \times 10^7$ | 2141 | 100 | 2141 | 5.5 |
| | | $8.6 \times 10^7$ | 1101 | 100 | 1101 | 2.8 |
| | | $1.0 \times 10^8$ | 2447 | 70 | 3496 | 9 |
| | | $2.7 \times 10^7$ | 690 | 83 | 831 | 2.1 |
| Fil− | pINA135 | $6.5 \times 10^6$ | 1744 | 87 | 2001 | 5.1 |

Measurement of the specific activity of beta-galactosidase in crude extracts. The cell density at the time of extraction is expressed as the number of cells per ml; the specific activity is in international units (one unit is defined as the amount of enzyme which hydrolyzes $10^{-9}$ moles per min of ortho-nitrophenol galactoside at 37° C.), and it is then corrected to take into account the percentage of prototrophs in the culture. A level of 1 is arbitrarily assigned to the mean of two measurements obtained with clones transformed with pINA98 (integrative plasmid). The zero level corresponds to strains transformed with pINA171 (LEU2+ars without lacZ). The different lines of results with pINA135 (replicative plasmid depicted in FIG. 9) in the Fil+ or Fil− strains correspond to independent transformants.

EXAMPLE 10

Isolation of Ars Sequences

In order to demonstrate that the isolation of ars sequences which are efficacious for *Y. lipolytica* was not dependent on the Fil− strain (morphological mutant), we had already shown that plasmids carrying an ars sequence could replicate in a Fil+ strain. We now sought to show that it was also possible to find ars sequences by directly transforming a Fil+ strain with the library of genes. In the first place, the same library was used (pool No. 2 of the latter), and from among the Leu+ transformants we selected some which were unstable (see Table VI). The plasmids which they harbor were isolated by transformation of *E. coli* with mini-preparations of total DNA of the yeast transformants. We found clones carrying ars18, previously isolated in the Fil− strain from this same pool. However, these clones were not strictly identical to plasmid pINA119 described initially, as a result of the fact that, during the construction of the library (fragments originating from a complete restriction of DNA of a wild-type strain with BglII and inserted into the BamHI site of pINA62, religation of several BglII fragments in one and the same plasmid could have taken place.

Not knowing whether the sequence AGATCT (BglII site) could form part of a possible ars consensus sequence for Y. lipolytica, we decided also to use another library constructed by partial digestion of the genome of a wild-type strain (W29) with Sau3A, selection of the fragments approximately 10–15 kb in size and cloning into the BamHI site of the same plasmid pINA62. This library, described in reference 14, is representative of the Y. lipolytica genome and has, moreover, enabled three Y. lipolytica genes to be obtained by directed integration in the chromosome. We used the non-restricted DNA of this library to transform the Fil+ strain and the Fil− strain. In this case, we again identified the clones which were unstable for the Leu+ phenotype. To this end, the transformants are cultured with two successive passages on a solid minimum medium supplemented with leucin, followed by streaking on this same medium to obtain isolated colonies, which are screened by replication on minimum media with and without leucin. We thereby obtained two new ars transformants, in the process of analysis. The corresponding sequences are designated ars* in Table VI, in which the results of the transformations carried out with both DNA libraries are collectively summarized.

These figures are much lower than those known in S. cerevisiae, and show that only a few sequences are capable of supporting autonomous replication in Y. lipolytica. However, these results clearly demonstrate the generality of the process for isolation of ars sequences in any strain of this species.

It is, moreover, clear to those versed in the art that the process which we used for isolating ars sequences which are efficacious in Y. lipolytica could be repeated with a DNA of any origin. By way of example, we have been able to show that the DNA of bacteriophage k contained (between positions 44972 bp and 48502 bp, Roberts R. J., 1987, Nucleic Acid Research, 15, r189–r217) an efficacious sequence of this kind.

EXAMPLE 11

Reduction and Characterization of the Ars Sequences

For the purpose of characterizing better the sequences described above, we carried out subclonings and deletions of the various plasmids pINA171, pINA123 and pINA124 (see FIGS. 6 and 7). The constructions made from the last two plasmids are depicted in FIG. 10, where it is seen that it is possible to localize the efficacious portion of both ars68 and ars77 on 2.7 kb and 2.4 kb fragments, respectively, which represents a very strong reduction in the size of DNA necessary for building ars vectors. In effect, the DNA insertions of Y.

TABLE VI

| Library | Experiment No. | Strain | Trans. frequency | Clones tested | Number unstable | % Unst. | ars found | % ars different |
|---|---|---|---|---|---|---|---|---|
|  |  |  | Pool |  |  |  |  |  |
| BglII | 1 | Fil− | 1  15T/1 g | 85 | 10 | 11.7 | ars68 |  |
| in |  |  | 2  300T/1 g | 76 | 12 | 15.8 | ars77 |  |
| pINA62 |  |  | 3  70T/1 g | 44 | 1 | 2.2 | ars18 |  |
|  |  |  | 4  10T/1 g | 13 | 0 | <7.6 | — |  |
|  |  | Overall Pool | 100T/1 g | 218 | 23 | 10.6 |  | 1.4% |
|  | 2 | Fil− | 2  200T/1 g | 25 | 3 | 12.0 | ars18 | 4.0% |
|  | 3 | Fil− | 2  100T/1 g | 181 | 6 | 3.3 | ars18 | 0.5% |
| Sau3A | 4 | Fil− | 200T/1 g | 44 | 1 | 2.2 | ars* | 2.2% |
| (partial in pINA62 |  | Fil− | 650T/1 g | 131 | 1 | 0.8 | ars* | 0.8% |

TABLE VI: Production of ars sequences in Fil+ or Fil− strains transformed with different genomic libraries. The name of the ars sequences found is indicated (ars* for the sequences in the process of characterization). The last column show the ratio consisting of the number of independent ars sequences found over the number of clones tested, for a given experiment.

TABLE VI: Production of ars sequences in Fil+ or Fil− strains transformed with different genomic libraries. The name of the ars sequences found is indicated (ars* for the sequences in the process of characterization). The last column shows the ratio consisting of the number of independent ars sequences found over the number of clones tested, for a given experiment.

If account is taken only of the genuinely different ars sequences isolated, it is seen that the latter are selected at a frequency of the order of 2.5% in a Fil− context and of the order of 0.6% in a Fil+ context, irrespective of the type of library used (Table VII)

|  | Library |  |
|---|---|---|
| Strain | BglII complete | Sau3A partial |
| Fil− | 2.7% | 2.2% |
| Fil+ | 0.5% | 0.8% |

Percentage of Leu+ clones possessing different ars sequences among the Y. lipolytica transformants obtained with the two genomic libraries, over all 4 experiments presented in Table VI.

lipolytica were initially 6.6 kb and 17.8 kb in size in plasmids pINA123 and pINA124, respectively.

Moreover, the same type of strategy led us to analyse the ars18 sequence. The plasmid constructions were carried out using plasmid pINA171 described above, or using pINA147, which is the mini vector of FIG. 8A. These two vectors contain the same 2.2 kb BamHI fragment which bears the ars activity, the same LEU2 marker gene (a 2.0 kb SalI-ApaI fragment in the case of pINA147 and, in the case of pINA171, the 5.3 kb SalI-SalI fragment which is also present in plasmid pINA62 (FIG. 4)). It differs in the bacterial portion, which consists of Bluescript (Stratagène, 3770 Tansy Street, San Diego, Calif. 92121) for pINA147 and of pBR322 for pINA171.

All the plasmid constructions were carried out by deletions or reclonings employing the restriction sites indicated in FIG. 11, except in the case of pINA211. The latter plasmid was obtained in the following manner, based on the descriptions of in vivo deletions observed in S. cerevisiae (15, 16): plasmid pINA147 was linearized with the enzyme ClaI, whose site is present in the Bluescript portion a few bases upstream from the ars; the yeast was transformed with the plasmid thus linearized; the clones which were unstable for the Leu+ phenotype were identified and the plasmids which they contained were extracted therefrom. This plasmid proved to contain a deletion of approximately 70 base pairs which is produced in vivo by the *Y. lipolytica* yeast before the latter religates this plasmid with itself so that it is then propagated in the state of a circular molecule.

As shown in FIG. 11, we were able to demonstrate that the sequences responsible for high frequency transformation and for extrachromosomal replication can be physically localized on two adjacent regions. To preserve the two functions, we decided to use the 1.3 kb fragment present in plasmid pINA176. This ars fragment is bounded by two BamHI sites, since ligation of the righthand Sau3A site to the BamHI site of the vector re-formed a BamHI site. This fragment could hence be inserted into other vectors based on pBR322, either in the BamHI site present in the gene coding for resistance to tetracycline (pINA232), or in the BglII site present in the terminal portion of the LEU2 sequence (pINA237 and pINA237'), or finally at the BglII site of a cloning multisite inserted at the PvuII site of the vector (pINA240 and pINA240'). The vectors pINA237, pINA240 and pINA240' are especially suitable since, when insertion of the ars has taken place at a BglII site, the BamHI sites of the insertion have disappeared.

These vectors consequently contain:
the 2 kb sequence permitting expression of the LEU2 gene;
the sequence of ars18, reduced to 1.3 kb;
the two genes for resistance to the antibiotics ampicillin and tetracycline;
a single BamHI site permitting cloning (especially of fragments originating from a partial digestion with Sau3A for the construction of a genomic library on a replicative plasmid of this kind) with identification of the hybrid clones as sensitive to tetracycline.

The maps of plasmids pINA176, pINA232, pINA237, pINA237', pINA240 and pINA240' are depicted in FIG. 12. All were tested for their capacity to transform the Fil+ strain INAG33122, and all can enable more than 5000 transformants to be obtained per 1 g of non-restricted DNA.

Moreover, the 1.3 kb fragment of ars18 was characterized further by its nucleotide sequence, established by Sanger's dideoxynucleotide method, on both strands. FIG. 13 shows this sequence of 1305 nucleotides, characterized by a richness in AT (67.5%) and by a complex profile of internal repetition of 10 to 13 bases, either in the direct or in the reverse orientation, the most significant of which are underlined. Since most of these are present in the portion of the sequence which we have shown above to be important for autonomous replication, it may be wondered whether they play a part in this function.

Gene Expression and Amplification by Means of the Ars Sequence

We showed previously the usefulness of the ars18 present on pINA119 for amplifying the lacZ gene of *E. coli*. We demonstrate here that this ars18 sequence permits amplification of the homologous XPR2 gene of *Y. lipolytica* coding for alkaline extracellular protease or AEP (17), of the heterologous SUC2 genes of *S. cerevisiae* coding for invertase (18), of the porcine pro-INF-al gene coding for interferon-a$_1$ (19) and of the pro-REN gene coding for bovine chymosin (19). The amplification of these genes enabled the production and secretion of the corresponding proteins to be increased. All the plasmids and strains used are depicted in FIG. 14 and described in Table VIII.

TABLE VIII

| PROTEIN SECRETED | PLASMID | CHARACTERISTIC | GENE | MARKER | STRAIN TRANSFORMED | RESULTING STRAIN |
|---|---|---|---|---|---|---|
| AEP | pINA157 | CHROMOSOMAL DISRUPTION | XPR2 xpr2::LYS5 | LYS5 | JM12 | JM12 JM23 |
|  | pINA136 | REPLICATIVE | XPR2 | LEU2 | JM23 | JM69,JM70 |
|  | pINA169 | INTEGRATIVE | SUC2 | LEU2 | JM23 | JM55 |
| INVERTASE | pINA181 | REPLICATIVE | SUC2 | LEU2 | JM23 | P1 |
| INTERFERON | pINA187 | INTEGRATIVE | proINFα | URA3 | JM23 | JM77 |
|  | pINA250 | REPLICATIVE | proINFα | LEU2 | JM23 | JM85–JM87 |
| CHYMOSINE | pLX34 | INTEGRATIVE | proREN | LEU2 | DL118 | DL249 |
|  | — | — | — | — | INAG33122 | LX2-1 |
|  | pINA184 | REPLICATIVE | proREN | LEU2 | DL118 | TF1,2,4,5 |
|  | — | — | — | — | INAG33122 | 2-36 |

Name of the integrative and replicative vectors used for amplification of the homologous XPR2 gene and of the heterologous SUC2, pro-INFα1 and pro-REN genes. The names of the receptor strains and of the transformants selected for assays of the various activities are also to be found in the last two columns.

EXAMPLE 12

Expression and Amplification of the XPR2 Gene

The XPR2 gene of *Y. lipolytica* coding for alkaline extracellular protease (AEP) was inserted into a replicative plasmid and then introduced into *Y. lipolytica*. We compared the production of alkaline extracellular protease secreted by the following strains of our collection:

JM12 (MatB, leu2-35, lys5-12, ura3-18, XPR2) was disrupted using plasmid pINA157 depicted in FIG. 14. This disruption is obtained by transformation of the strain JM12 with plasmid pINA157 previously restricted with the restriction enzymes MluI and EcoRI. According to the principle shown in FIG. 15, we obtained, by double crossing over, the replacement of the XPR2 gene for the LYS5 gene. The resulting strain JM23 is hence isogenic with the strain JM12 with the exception of the marker LYS5 and the disrupted gene XPR2. This strain, no longer producing alkaline extracellular protease, is a good receptor for the production of proteins. We transformed this strain, isogenic with JM12, with the replicative plasmid pINA136. JM69 and JM70 correspond to the strain JM23 transformed by the replicative plasmid pINA136.

The comparison of the amount of AEP secreted by the strains JM12, JM23, JM69 and JM70 is shown in Table IX, which demonstrates that a corrected amplification by a factor 3.4 to 5.6 can be obtained with ars18. This corrected amplification factor takes into account the percentage of Leu+ cells in the culture at the time of the assay, as already explained above for the assay of α-galactosidase.

TABLE IX

| Strain | Plasmid | Cell density (Klett) | Activity | % LEU+ | Corrected amplification |
|---|---|---|---|---|---|
| JM23 | pINA157 in JM12 | 475 | 0 | 100 | — |
| JM12 | no plasmid | — | 100 | 100 | 1 |
| JM69 | pINA136 in JM23 | — | 274 | 80 | 3.4 |
| JM70 | pINA136 in JM23 | — | 446 | 80 | 5.6 |

Comparison of the production of protease activity secreted by the disrupted strain JM23, the strain JM12 which possesses a chromosomal copy of the XPR2 gene and the transformants JM69 and JM70 which possess the XPR2 gene on a replicative plasmid. Culturing is carried out at 28° C. in GPP medium (glycerol 6.7 g/l, Yeast Nitrogen Base without ammonium sulfate 1.7 g/l, glutamate 1 g/l, proteose peptone 1.7 g/l, 50 mM phosphate buffer pH 6.8). The culture was inoculated with 10 Klett units and the supernatant was withdrawn 23 hours after the inoculation. The protease activity determined according to the method of Donnelly et al. (27), and is expressed here in arbitrary units. The percentage of Leu+ cells is determined by plating an aliquot of the culture on medium supplemented with leucine, followed by replication on media with and without leucine. The corrected amplification is calculated with the activities corrected by the percentage of Leu+ cells.

The promoter of the XPR2 gene possesses a complex regulation (Ogrydziak et al. (21)). The kinetics and the levels of production depend on the medium and on the culture conditions. We hence compared the kinetics of production of the strain JM12 and the strain JM70 in non-inducing YNB medium (Yeast Nitrogen Base without ammonium sulfate 1.7 g/l, sodium glutamate 1 g/l, glucose 10 g/l, 50 mM phosphate buffer pH 6.8) and in two inducing media YNBpp (YNB to which 1.7 g/l of proteose peptone is added) and YPDm (yeast extract 1 g/l, proteose peptone 50 g/l, glucose 10 g/l). The protease activity was measured with azocoll (Sigma A8143) as substrate (10 mg/ml in 50 mM Tris, pH 8), measuring the increase in absorbance at 520 nm after incubation for 30 minutes at 30° C.

The results are shown in FIG. 16 and Table X.

of 50. This phenomenon, still unexplained, should enable the regulatory element to be identified and hence suggests that there are other possibilities of amplification of expression which remain little exploited.

EXAMPLE 13

Expression and Amplification of the SUC2 Gene

The SUC2 gene of *S. cerevisiae* coding for invertase (18) was placed under the control of the XPR2 promoter and fused to the signal sequence of alkaline extracellular protease (see FIG. 17). We compared the production of invertase in two strains:

JM55, which corresponds to the strain JM23 transformed with the integrative plasmid pINA169 integrated at the XPR2 site. The integration is directed to the XPR2 site, since plasmid pINA169 was restricted beforehand with the restriction enzyme NheI, whose single cleavage site is in the XPR2 region.

P1, which corresponds to the strain JM23 transformed with the replicative plasmid pINA181.

The invertase activity was measured by the method of Werner et al. (22). The amplification of the invertase production was measured in inducing YPDm medium, in which the source of carbon is sucrose (10 g/l) or glucose (10 g/l). The results are illustrated in FIG. 18. After 40 hours of culture, we obtained an uncorrected amplification factor (that is to say, considering that all the cells are productive) of 2 to 2.9 in glucose or sucrose. It may be noted that this construction enables *Y. lipolytica* to grow on a medium containing sucrose as a source of carbon, which hence represents a new substrate for this organism.

EXAMPLE 14

Expression and Amplification of the ProINF-α1 Gene

The porcine pro-INF-α1 gene coding for interferon-α1 having antiviral activity, was placed under the control of the XPR2 promoter and fused to the "prepro" portion of AEP (for the construction, see FIG. 19). We compared the production of interferon produced by the strain possessing a copy of the gene integrated at the XPR2 site (JM85 to JM87) possessing the gene on a replicative plasmid (pINA250):

the strain JM77 corresponds to the strain JM23 transformed with plasmid pINA187 previously restricted

TABLE X

| STRAIN | PLASMID | CHARACTERISTIC | MEDIUM | EPA ACTIVITY | % LEU+ | CORRECTED AMPLIFICATION |
|---|---|---|---|---|---|---|
| JM12 | — | CHROMOSOMAL | YNB | 0.08 | 100% | 1 |
| JM12 | — | CHROMOSOMAL | YNBpp | 4.2 | 100% | 1 |
| JM12 | — | CHROMOSOMAL | YPDm | 12.2 | 100% | 1 |
| JM70 | pINA136 | REPLICATIVE | YNB | 3.4 | 81.6% | 52 |
| JM70 | pINA136 | REPLICATIVE | YNBpp | 12 | 84.6% | 3.4 |
| JM70 | pINA136 | REPLICATIVE | YPDm | 60.2 | 83.6% | 5.9 |

Activity values obtained 40 hours after inoculation. The protease activity is in arbitrary units.

The amplification factor obtained at time 40 h after the inoculation varies between 3.4 and 5.9 for the cultures prepared on inducing medium. In contrast, in repressing medium (YNB), evasion of regulation probably takes place in the case of the replicative transformants, thereby explaining an amplification by a factor with the restriction enzyme MluI, whose single cleavage site is in the XPR2 region;
the strains JM85, JM86 and JM87 correspond to the strain JM23 transformed with the replicative plasmid pINA 250.

The results shown in Table XI show that the corrected amplification by a factor of 3.75 to 8.2 can be obtained with ars18.

TABLE XI

| STRAIN | PLASMID | CHARACTERISTIC | MEDIUM | INFa ACTIVITY | % LEU+ | CORRECTED AMPLIFICATION |
|---|---|---|---|---|---|---|
| JM77 | pINA187 | INTEGRATIVE | YPDm | 100 | 100% | 1 |
| JM85 | pINA250 | REPLICATIVE | YPDm | 300 | 49% | 6.1 |
| JM86 | pINA250 | REPLICATIVE | YPDm | 300–225 | 36% | 8.2–6.2 |
| JM87 | pINA250 | REPLICATIVE | YPDm | 225 | 60% | 3.75 |

Comparison of the production of antiviral activity secreted by the strain JM77, which possesses a chromosomal copy of the hybrid gene XPR2-INFα1, and the transformants JM85, JM86 and JM87, which possess the XPR2-INFα1 gene on a replicative plasmid. Culturing is carried out at 20° C. in YPDm medium (yeast extract 1 g/l, proteose peptone 50 g/l, glucose 10 g/l). The culture is inoculated with 10 Klett units and the supernatants were withdrawn 48 and 53 hours after the inoculation. The antiviral activity is determined according to the method described by la Bonnardière and Laure (28), and is expressed here in arbitrary units.

EXAMPLE 15

Expression and Amplification of the Gene Coding for Prochymosin

The production of prochymosin by *Y. lipolytica* yeast has already been documented in the patent cited as reference 23 and in the publication by Franke et al. (20), in which the integrated plasmid LEU2-proREN has been described. This plasmid, referred to as pLX34, is shown in FIG. 14. It possesses the proREN gene under the control of the promoter of the LEU2 gene of *Y. lipolytica*. The production of chymosin was compared in:

the strain DL 249, which harbors pLX34 integrated at the bio genomic locus;

the strain DL118, which is isogenic therewith, and which was transformed with plasmid pINA184. The latter is derived from pLX34 by the attachment of ars18 (FIG. 14). Transformants producing prochymosin and having the unstable Leu+ phenotype were selected and cultured on liquid medium at 23° C.

Table XII shows that, after 60 hours of culture on YNBS minimum medium (yeast nitrogen base 6.7 g/l, glucose 10 g/l), chymosin production is higher in the replicative transformants than in the integrative control by a factor of 1.3.

Assay of chymosin activity present in culture supernatants of different transformants of *Y. lipolytica*. The activity is expressed in arbitrary units. For the assay, the method described in reference (20) was followed; after centrifugation of the cells, the supernatant was activated by treatment for 20 minutes at approximately pH 2 (with hydrochloric acid) in order to convert the zymogen to active chymosin. The activity of the latter was measured by its capacity to curdle 1 ml of milk (12% Difco skim milk in 41.5 mM sodium acetate pH 6.5, 13.6 mM calcium chloride) at 37° C. by comparison with a standard series of commercial rennin (Sigma R 4879).

If this production is referred to the cells which possess the plasmid on minimum medium (average value of 70%), an amplification factor of 1.77 is found.

The same experiment was carried out by transforming the strain INAG33122 (Fil+), described above, with the same plasmids pLX34 (integration directed to the LEU2 genomic locus by linearization of the plasmid with the enzyme XhoI and pINA184 (replicative plasmid). The transformants were cultured on YEPG complete medium (yeast extract 0.1%, peptone 5%, glucose 1%). After 50 hours of culture at 23° C., chymosin production in the medium was again found to be 1.3 times as high in the replicative transformant as in the integrative transformant. After correction by the percentage of Leu+ cells observed at this stage of culturing (45%), it is found that the amplification produced is by a factor of 2.8.

The following strains were deposited on 21 January 1988 at the Collection Nationale de Cultures de Microorganismes (National Collection of Microorganism Cultures) of the Institut Pasteur, 28 rue du Docteur-Roux 75724 Paris Cèdex 15:

*Escherichia coli*: INAG 20 580/pINA123 under No. I-724

*Yarrowia lipolytica*: INAG 33 129 under No. I-725

*Yarrowia lipolytica*: INAG 33462/pINA119 under No. I-726.

IFN-alpha$_1$ gene and antibodies have been communicated from Claude La Bonnardière, Institut National de la Recherche Agronomique, Jouy-en-Josas and the biologic dosages of IFN have been done in his laboratory.

Complementary experiments on amplification of SUC2, IFN-alpha$_1$ and protease have been made with the help of Jean-Marc Nicaud.

TABLE XII

| RECEPTOR | TRANSFORMANT | PLASMID | MODE | MEDIUM | CHYMOSIN ACTIVITY | | % LEU+ | CORRECTED AMPLIFICATION |
|---|---|---|---|---|---|---|---|---|
| DL118 | DL249 | pLX34 | Integrative | YNBS | 1.0 | | 100% | |
|  | TF1 | pINA184 | Replicative | — | 1.26 | | 70% | |
|  | TF2 | — | — | — | 1.23 | Mean: | — | |
|  | TF4 | — | — | — | 1.29 | 1.24 | — | 1.77 |
|  | TF5 | — | — | — | 1.18 | | — | |
| INAG33122 | LX2-1 | pLX34 | Integrative | YEPG | 1.0 | | 100% | |
|  | 2-36 | pINA184 | Replicative | — | 1.28 | | 45% | 2.84 |

BIBLIOGRAPHIC REFERENCES

1. Williamson D. H.: Yeast, 1985, 1, (1-2), 1–14.
2. Kearsey S.: Bio Essays, 4, (4), 157–161.
3. Gaillardin C., Ribet A-M. and Heslot H.: Curr. Genet., 1985, 10, 49–58.
4. Davidow, L. S., Apostolakos D., O'Donnell M. M., Proctor A. R., Ogrydziak D. M., Wing R. A., Stasko I. and De Zeeuw J. R.: Curr. Genet., 1985, 10, 39–48.

5. Gaillardin C. and Ribet A-M.: Curr. Genet., 1987, 11, 369-375.
6. Wing R. A. and Ogrydziak D. M.: In Molecular Genetics of Filamentous Fungi, Timberlake W. E. (Ed.), UCLA Symposia vol. 34, 1985, 367-382.
7 Murray A. W. and Szostak J. W.: Cell, 1983, 34, 961-970.
8. Davidow L. S. and De Zeeuw J. R.: European Patent Publication Number 0,138,508-Al, 1984.
9. Fournier P., Gaillardin C., Persuy M-A., Klootwijk J. and van Heerikhuizen H.: Gene, 1986, 42, 273-282.
10. Southern E. M.: J. Mol. Biol., 1975, 98, 503.
11. Chan C. S. M. and Tye B-K.: J. Mol. Biol., 1983, 168, 505-523.
12. Miller J. H.: In Experiments in Molecular Genetics. Cold Spring Harbor Laboratory, Cold Spring Harbor, 1971.
13. Bradford H. M.: Anal. Biochem., 1976, 72, 248.
14. Xuan J., Fournier P. and Gaillardin C.: Cloning of the LYS5 gene encoding saccharopine dehydrogenase from the yeast *Yarrowia lipolytica* by target integration. Curr. Genet. 14: 15-21 (1988).
15. Orr Weaver T. and Szostak J.: Yeast recombination: the association between double-strand gap repair and crossing-over. Proc. Natl. Acad. Sci. 80: 4417-4421 (1983).
16. Kunes S., Botstein D. and Fox M.: Transformation of yeast linearized DNA formation of inverted dimers and recombinant plasmid products. J. Mol. Biol. 184: 375-387 (1985).
17. Davidow L., O'Donnell M., Kaczmarek F., Pereira D., De Zeeuw J. and Franke A.: Cloning and sequencing of the alkaline extracellulaire protease gene of *Y. lipolytica*. J. Bacteriol. 169: 4621-4629 (1987).
18. Taussig R. and Carlson M.: Nucleotide sequence for the yeast SUC2 gene for invertase. Nucleic Acids Res. 11: 1943-1954 (1983).
19. Lefevre F. and la Bonnardière C.: Molecular cloning and sequencing of a gene encoding biologically active porcine interferon. J. of Interferon Research 6: 349-360 (1986).
20. Franke A., Kaczmarek F., Eisenhard M., Geoghegan K., Danley D., De Zeeuw J., O'Donnell M., Gollaher M. and Lance S.: Expression and secretion of bovine prochymosin in *Yarrowia lipolytica*. Dev. in Industrial microbiology 29: 43-57 (1988).
21. Ogrydziak D., Demain A. and Tannenbaum S.: Regulation of extracellular protease production in *Candida lipolytica* Biochim. Bioph. Acta 497: 525-538 (1977).
22. Werner W., Rey H. and Wielinger H. Z.: Analyt. Chem. 252: 224 (1970).
23. Davidow L., Franke A. and De Zeeuw J.: Expression and secretion of heterologous proteins by *Yarrowia lipolytica*. transformants. European Patent Application 86-307839, 1986.
24. Kikuchi Y.: Yeast plasmid requires a cis-acting locus and two plasmid proteins for its stable maintenance. Cell 35: 487-493 (1983).
25. Wolf-Dietrich H., Sipiczki M. and Kohli J.: Replicating plasmids in *Schizosaccharomyces pombe*: improvement of symmetric segregation by a new genetic element. Mol. Cell. Biol. 6: 80-89 (1986).
26. Williamson D.: The yeast ARS element, six years on: a progress report. Yeast 1: 1-14 (1985).
27. Donnelly et al.: $^{14}$C methylated β casein as a substrate for plasmin and its application to the study of milk protein transformations. B.B.A. 626: 117-126 (1980).
28. La Bonnardière and Laude H.: High interferon titer in newborn pig intestine during experimentally induced viral enteritis. Infect. Immun. 32: 28-31 (1981).

We claim:

1. An isolated ars sequence from *Yarrowia lipolytica* which is efficacious in *Yarrowia lipolytica*.

2. The ars sequence of claim 1, comprised in the 2.2 kb (BamHI/BamHI) DNA fragment possessing the restriction map of FIG. 8B.

3. The ars sequence as claimed in claim 1, which corresponds to the efficacious portion of the sequence depicted in FIG. 13.

4. DNA comprising an ars sequence as claimed in one of claims 1 to 3.

5. A plasmid comprising an ars sequence as claimed in one of claims 1 to 3.

6. A plasmid comprising an ars sequence according to claim 1, which is obtained by a process comprising:
   a) forming a library of genomic fragments of *Y. lipolytica* in an integrative vector complementing an auxotrophy of *Y. lipolytica*;
   b) transforming a host strain of *Y. lipolytica*, possessing an auxotrophy capable of being complemented by said integrative vector, with plasmids of said library;
   c) colony hybridizing with a probe which detects said integrative vector, wherein transformants possessing the strongest hybridization signal are selected;
   d) preparing a minilysate of vector clones and detecting extrachromosomal plasmids; wherein
   e) said plasmids having at least 5 times greater power of transformation as compared to that of the original vector are identified as plasmids comprising an ars sequence.

7. The plasmid as claimed in claim 6, wherein said library is formed in an integrative vector of pINA62 type and said host strain is a Fil+ strain capable of being transformed with supercoiled circular plasmids of said library whereby LEU+ transformants are selected by colony hybridization with a pBR322 probe and potential ars clones are isolated; whereby
   minilysates of the clones are selected and extrachromosomal plasmids are detected with a pBR322 probe and plasmids comprising an ars sequence are identified; whereby *E. coli* is transformed with DNA of said minilysates, and said plasmids identified as comprising an ars sequence are amplified to enable expression of an industrial protein in *Y. lipolytica*.

8. The plasmid of claim 7, wherein said LEU+ transformants contain an integrated plasmid.

9. The plasmid of claim 7, wherein said LEU+ transformants contain a replicative plasmid.

10. The plasmid of claim 7, wherein said minilysates of the clones are selected by Southern transfer of non-restricted DNA.

11. The plasmid as claimed in claim 7, wherein, for a Fil− host strain, the instability of the transformants is tested and the transformants possessing the lowest stability are selected.

12. A DNA sequence comprising an ars sequence obtained from a plasmid as claimed in one of claims 6 and 11.

13. A plasmid containing an integration vector complementing an auxotrophy of *Y. lipolytica* containing an ars sequence which is efficacious in *Y. lipolytica*.

14. A plasmid for the expression of an industrial protein in *Y. lipolytica*, which contains all the elements enabling provision to be made for the expression of the said protein in *Y. lipolytica*, and which contains an ars sequence isolated from *Yarrowia lipolytica*.

15. The plasmid as claimed in claim 14, wherein said plasmid comprises the sequence coding for the said protein under the control of a *Y. lipolytica* promoter.

16. The plasmid as claimed in claim 15, wherein the promoter is the XPR2 or LEU2 promoter.

17. The plasmid as claimed in claim 16, wherein the protein is chosen from AEP, invertase, porcine interferon-$\alpha_1$ and prochymosin.

18. The plasmid as claimed in claim 17, which contains the XPR2 gene of *Y. lipolytica*.

19. The plasmid as claimed in claim 17, which contains the SUC2 gene of *S. cerevisiae* under the control of the XPR2 promoter.

20. The plasmid as claimed in claim 19, wherein the SUC2 gene is fused to the signal sequence of alkaline extracellular protease.

21. The plasmid as claimed in claim 18, wherein the proREN gene is under the control of the promoter of the LEU2 gene of *Y. lipolytica*.

22. The strain of *Y. lipolytica* transformed by a plasmid as claimed in one of claims 5, 11 and 13 to 21.

23. The strain as claimed in claim 22, wherein the plasmid contains at least one heterologous sequence.

24. The strain as claimed in one of claims 22 and 23, which is a Fil+ strain.

25. The strain as claimed in one of claims 22 and 23, which is a Fil− strain.

* * * * *